US012343350B2

(12) United States Patent
Bianchi et al.

(10) Patent No.: US 12,343,350 B2
(45) Date of Patent: Jul. 1, 2025

(54) ISTAROXIME-CONTAINING INTRAVENOUS FORMULATION FOR THE TREATMENT OF ACUTE HEART FAILURE (AHF)

(71) Applicant: Windtree Therapeutics, Inc., Warrington, PA (US)

(72) Inventors: Giuseppe Bianchi, Milan (IT); Patrizia Ferrari, Varese (IT); Mara Ferrandi, Milan (IT); Paolo Barassi, Castelveccana (IT)

(73) Assignee: Windtree Therapeutics, Inc., Warrington, PA (US)

( * ) Notice: Subject to any disclaimer, the term of this patent is extended or adjusted under 35 U.S.C. 154(b) by 58 days.

(21) Appl. No.: 18/150,870

(22) Filed: Jan. 6, 2023

(65) Prior Publication Data
US 2023/0293548 A1 Sep. 21, 2023

Related U.S. Application Data

(63) Continuation of application No. 17/517,530, filed on Nov. 2, 2021, now Pat. No. 11,583,540, which is a continuation of application No. 17/233,302, filed on Apr. 16, 2021, now Pat. No. 11,197,869, which is a continuation of application No. PCT/US2019/060961, filed on Nov. 12, 2019.

(60) Provisional application No. 62/814,149, filed on Mar. 5, 2019.

(51) Int. Cl.
| | |
|---|---|
| *A61K 31/5685* | (2006.01) |
| *A61K 9/00* | (2006.01) |
| *A61P 9/04* | (2006.01) |
| *A61P 9/06* | (2006.01) |

(52) U.S. Cl.
CPC .......... *A61K 31/5685* (2013.01); *A61K 9/009* (2013.01); *A61P 9/04* (2018.01); *A61P 9/06* (2018.01)

(58) Field of Classification Search
CPC ....... A61K 31/5685; A61K 9/009; A61P 9/06; A61P 9/04
See application file for complete search history.

(56) References Cited

U.S. PATENT DOCUMENTS

| | | | |
|---|---|---|---|
| 4,534,899 A | 8/1985 | Sears | |
| 5,846,743 A | 12/1998 | Janmey et al. | |
| 5,874,268 A | 2/1999 | Meyer | |
| 6,007,839 A | 12/1999 | Mayhew et al. | |
| 6,063,400 A | 5/2000 | Geho et al. | |
| 6,261,815 B1 | 7/2001 | Meyer | |
| 6,384,250 B2 | 5/2002 | Gobbini | |
| 6,589,503 B1 | 7/2003 | Piwnica-Worms | |
| 7,109,034 B2 | 9/2006 | Orwar et al. | |
| 7,306,783 B2 | 12/2007 | Piwnica-Worms | |
| 2004/0028670 A1 | 2/2004 | Carlson et al. | |
| 2004/0151766 A1 | 8/2004 | Monahan et al. | |
| 2005/0136121 A1 | 6/2005 | Kershman et al. | |
| 2006/0083737 A1 | 4/2006 | Minomi et al. | |
| 2007/0042031 A1 | 2/2007 | Maclachlan et al. | |
| 2007/0077286 A1 | 4/2007 | Ishihara et al. | |
| 2007/0082042 A1 | 4/2007 | Park et al. | |
| 2007/0110798 A1 | 5/2007 | Drummond et al. | |
| 2010/0087374 A1 | 4/2010 | Ahmad et al. | |
| 2010/0087500 A1 | 4/2010 | Stover | |
| 2016/0151461 A1 | 6/2016 | Shannon | |

FOREIGN PATENT DOCUMENTS

| | | |
|---|---|---|
| CN | 103316968 B | 4/2015 |
| EP | 0825197 B1 | 2/1998 |
| WO | WO 2014/086870 A1 | 5/2014 |

OTHER PUBLICATIONS

Gobbini et al., 18 Bioorg. Med. Chem. 4275-4299 (2010) (Year: 2010).*
Lanoxin ® Prescribing Information (Revised Feb. 2019) (Year: 2019).*
Abraham et al., "In-hospital mortality in patients with acute decompensated heart failure requiring intravenous vasoactive medications: an analysis from the Acute Decompensated Heart Failure National Registry (ADHERE)" J Am Coll Cardiol 46:57-64 (2005).
Alemanni et al. "Role and mechanism of subcellular Ca2+ distribution in the action of two inotropic agents with different toxicity" J Mol Cell Cardiol 50:910-8 (2011).
Al-Muhammed, "In-vivo studies on dexamethasone sodium phosphate liposomes" J. Microencapsul. 13:293-306 (1996).
Asahi et al., "Transmembrane helix M6 in sarco(endo)plasmic reticulum Ca(2+)-ATPase forms a functional interaction site with phospholamban. Evidence for physical interactions at other sites" J Biol Chem 274: 32855-32862 (1999).
Ashkar & Makaryus, "Dobutamine", In StatPearls [Internet], Treasure Island (FL): SlatPearls Publishing, Jan. 2017-Jan. 2018 (available at https://www.ncbi.nlm.nih.gov/books/NBK470431/).
Baheti et al., "Excipients used in lyophilization of small molecules" J. Excipients and Food Chem. 1(1):41-54 (2010).
Bers et al., "Regulation of Ca2+ and Na+ in normal and failing cardiac myocytes" Ann N.Y. Acad Sci 2006; 1080:165-177 (2006).
Bers, "Altered cardiac myocyte Ca regulation in heart failure" Physiology 21: 380-387 (2006).

(Continued)

*Primary Examiner* — Timothy R Rozof
(74) *Attorney, Agent, or Firm* — Kathleen D. Rigaut; Howson & Howson, LLP

(57) ABSTRACT

Compositions for intravenous infusion of istaroxime, or a metabolite of istaroxime, in human patients suffering from heart failure are disclosed. Likewise, methods for extended infusion of istaroxime or its metabolites in individuals with heart failure are disclosed. In particular, some methods disclosed herein include the infusion of istaroxime, or a metabolite thereof, for a period of time that is greater than six hours in order to improve cardiac relaxation without triggering arrhythmogenic events in an individual suffering from heart failure. Other methods include administration of istaroxime until certain plasma concentration thresholds of istaroxime metabolites are achieved. Also disclosed are istaroxime metabolites with selective SERCA2a activation.

19 Claims, 3 Drawing Sheets

(56) References Cited

OTHER PUBLICATIONS

Bers, "Calcium cycling and signaling in cardiac myocytes" Annu Rev Physiol 70:23-49 (2008).
Braunwald, "The war against heart failure: the Lancet lecture" 2015; 385:812-24 (2015).
Brophy et al., "Bioavailability of oral dexamethasone during high dose steroid therapy in neurological patients" Eur. J. Clin. Pharmacol. 24:103-108 (1983).
Bonsu et al., "Pharmacological treatments for heart failure with preserved ejection fraction—a systematic review and indirect comparison" Heart Failure Reviews 23:147-156 (2018).
Butler et al., Past, present, and future of acute heart failure clinical trials—a high-risk population in search of a strategy Eur J Heart Fail.20(5):839-841 (2018).
Byrne et al., "Recirculating cardiac delivery of AAV2/1SERCA2a improves myocardial function in an experimental model of heart failure in large animals" Gene Therapy 15:1550-1557 (2008).
Campla et al. "Acute Heart Failure with Low Cardia Output: Can We Develop a Short-term Inotropic Agent that Does Not Increase Adverse Events?" Curr. Heart Fall. Rep. 7:100-109 (2010).
Carillion et al., "Atorvastatin reduces β-Adrenergic dysfunction in rats with diabetic cardiomyopathy" PloS One e0180103 (2017).
Choi et al., "Defective intracellular Ca2+ signaling contributes to cardiomyopathy in Type 1 diabetic rats" Am. J. Physiol. Heart Cir. Physiol 283:H1398-H1408 92002).
Chonn & Cullis, "Recent advances in liposomal drug-delivery systems" Curr, Opin. Biotechnol. 6:698-708 (1995).
De Munari et al., "Structure-based design and synthesis of novel potent Na+, K+-ATPase inhibitors derived from a 5alpha, 14alpha-androstane scaffold as positive inotropic compounds" J. Med. Chem. 46(17): 3644-3654 (2003).
Do Carmo et al., "Chronic central leptin infusion restores cardiac sympathetic-vagal balance and baroreflex sensitivity in diabetic rats" Am. J. Physiol. Heart Cir. Physiol 295:H1974-1981 (2008).
Evangelista et al., "European Association of Echocardiography recommendations for standardization of performance, digital storage and reporting of echocardiographic studies" Eur J Echocardiogi 9(4):438-48 (2008).
Fernandez-Tenorio & Niggli, "Stabilization of Ca 2+ signaling in cardiac muscle by stimulation of Serca" J Mol Cell Cardiol. 119:87-95 (2018).
Ferrandi et al., "Renal Na,K-ATPase in genetic hypertension" Hypertension 28(6):1018-25 (1996).
Ferrandi et al., "Istaroxime stimulates SERCA2a and accelerates calcium cycling in heart failure by relieving phospholamban inhibition" Br J Pharmacol 169:1849-61 (2013).
Flaherty et al., "Acute heart failure syndromes in patients with coronary artery disease early assessment and treatment" J Am Coll Cardiol. 53(3):254-63 (2009).
Fotherby, "Bioavailability of orally administered sex steroids used in oral contraception and hormone replacement therapy" Contraception 54:59-69 (1996).
Georghiade et al., "Hemodynamic, Echocardiographic, and Neurohormonal Effects of Istaroxime, a Novel Intravenous Inotropic and Lusitropic Agent" J Am Coll Cardiol.51:2276-85 (2008).
Ghio et al., "Independent and additive prognostic value of right ventricular systolic function and pulmonary artery pressure in patients with chronic heart failure" J Am Coll Cardiol 37(1):183-8 (2001).
Gong et al., "Levosimendan Treatment for Heart Failure: A Systematic Review and Meta-Analysis" J Cardiothorac Vasc Anesth 29:1415-25 (2015).
Größl et al., "A novel artificial microRNA expressing AAV vector for phospholamban silencing in cardiomyocytes improves Ca2+ uptake into the sarcoplasmic reticulum" PLoS One 9:e92188 (2014).
Guido et al., "The Effects of Diabetes Induction on the Rat Heart: Differences in Oxidative Stress, Inflammatory Cells, and Fibrosis between Subendocardial and Interstitial Myocardial Areas" Oxid Med Cell Longev.2017: 5343972 (Epub Jul. 11, 2017).

Gulati et al., "Mitral annular descent velocity by tissue Doppler echocardiography as an index of global left ventricular function" Am J Cardiol. 77(11):979-84 (1996).
Haddad et al., "Right ventricular function in cardiovascular disease, part II: pathophysiology, clinical importance, and management of right ventricular failure" Circulation 117(13):1717-31 (2008).
Heineke & Molkentin, "Regulation of cardiac hypertrophy by intracellular signalling pathways" Nat Rev 7:589-600 (2006).
Hidalgo-Aragones et al., "Pharmacokinetics of oestrone-3-O-sulphamate" Steroid Biochem. Mol. Biol. 58:611-617 (1996).
Hoshijima et al., "Chronic suppression of heart-failure progression by a pseudophosphorylated mutant of phospholamban via in vivo cardiac rAAV gene delivery" Nat. Med. 8:864-871 (2002).
Hougen & Friedman, "Age-related effects of digoxin on myocardial contractility and Na-K pump in sheep" Am J Physiol. 243(4):H517-22 (1982).
Hulot et al., "Effect of intracoronary administration of AAV1/SERCA2a on ventricular remodelling in patients with advanced systolic heart failure: results from the AGENT-HF randomized phase 2 trial" Eur Heart J 19:1534-1541 (2016).
Iwanaga et al., "Chronic phospholamban inhibition prevents progressive cardiac dysfunction and pathological remodeling after infarction in rats" J Clin Invest 113, 727-736 (2004).
Joffe et al., "Abnormal cardiac function in the streptozotocin-induced non-insulin-dependent diabetic rat: noninvasive assessment with doppler echocardiography and contribution of the nitric oxide pathway" JACC 34(7):2111-2119 (1999).
Johnson et al., "Permeation of steroids through human skin" J. Pharm. Sci. 84:1144-1146 (1995).
Jørgensen, "Purification of Na+,K+-ATPase: enzyme sources, preparative problems, and preparation from mammalian kidney" Methods Enzymol. 156:29-43 (1988).
Kaneko et al., "A pyridone derivative activates SERCA2a by attenuating the inhibitory effect of phospholamban" Eur J Pharmacol 814:1-7 (2017).
Karim et al., "Phosphorylation-dependent conformational switch in spin-labeled phospholamban bound to SERCA" J Mol Biol 358:1032-1040 (2006).
Kaye et al., "Percutaneous cardiac recirculation-mediated gene transfer of an inhibitory phospholamban peptide reverses advanced heart failure in large animals" J. Am. Coll. Cardiol. 50:253-260 (2007).
Lancellotti et al., "European Association of Echocardiography recommendations for the assessment of valvular regurgitation. Part 2: mitral and tricuspid regurgitation (native valve disease)" Eur J Echocardiogr 11(4):307-32 (2010).
Lang et al., "Recommendations for chamber quantification: a report from the American Society of Echocardiography's Guidelines and Standards Commillee and the Chamber Quantification Writing Group, developed in conjunction with the European Association of Echocardiography, a branch of the European Society of Cardiology" J Am Soc Echocardiogr 18(12):1440-63 (2005).
Lipskaya et al., "Sarcoplasmic reticulum Ca(2+) ATPase as a therapeutic target for heart failure" Expert Opin Biol Ther 10:29-41 (2010).
Lloyd-Jones et al., "Lifetime risk for developing congestive heart failure: the Framingham Heart Study" Circulation 106:3068-3072 (2002).
Lohse et al., "What is the role of beta-adrenergic signaling in heart failure?" Circ Res 93:896-906 (2003).
Luciani et al., "Development and physico-chemical characterization of a liposomal formulation of istaroxime" Eur J Pharm Biopharm. 79(2):285-93 (2011).
MacLennan & Kranias, "Phospholamban: a crucial regulator of cardiac contractility" Nat Rev Mol Cell Biol 4(7):566-577 (2003).
Mann & Bristow, "Mechanisms and models in heart failure: the biomechanical model and beyond" Circulation 111:2837-2849 (2005).
Mattera et al., "Istaroxime: a new luso-inotropic agent for heart failure" Am J Cardiol 99(2A):33A-40A (2007).
Metra & Teerlink, "Heart failure" Lancet 390:1981-1995 (2017).
Micheletti et al., "Pharmacological profile of the novel inotropic agent (E,Z)-3-((2-aminoethoxy)imino)androstane-6,17-dione hydrochloride (PST2744)" J Pharmacol Exp Ther 303:592-600 (2002).

(56) References Cited

OTHER PUBLICATIONS

Micheletti et al., "Istaroxime, a stimulator of sarcoplasmic reticulum calcium adenosine triphosphatase isoform 2a activity, as a novel therapeutic approach to heart failure" Am J Card 99(2A):24A-32A (2007).
Mihm et al., "Diabetes related cardiomyopathy time dependent echocardiographic evaluation in an experimental rat model" Life Sci. 69(5):527-42 (2001).
Minamisawa et al., "Chronic phospholamban-sarcoplasmic reticulum calcium ATPase interaction is the critical calcium cycling defect in dilated cardiomyopathy" Cell 99:313-322 (1999).
Mitter et al., "A Test in Context: E/A and E/e' to Assess Diastolic Dysfunction and LV Filling Pressure" JACC 69(11):1451-1464 (2017).
Nagueh et al., "Recommendations for the evaluation of left ventricular diastolic function by echocardiography" Eur J Echocardiogr 10(2):165-93 (2009).
Nakayama et al., "Ca2+-and mitochondrial-dependent cardiomyocyte necrosis as a primary mediator of heart failure" J Clin Invest 117:2431-44 (2007).
Nediani et al., "Stimulation of cardiac sarcoplasmic reticulum calcium pump by acylphosphatase. Relationship to phospholamban phosphorylation" J Biol Chem. 271:19066-73 (1996).
Nicholson & Turner, "Marine steroids. Part III. On the structure of marthasterone glucoside from the starfish Marthasterals glacialls" J. Chem. Soc. Perkin Trans. 1(12):1357-1360 (1976).
No Author listed, "An Account of the Effects of the Digitalis Purpurea in Dropsy" Lond Med J. 6(Pt 1):55-60 (1785).
Ostro & Cullis, "Use of liposomes as injectable-drug delivery systems" Am. J. Hosp. Pharm. 46:1576-1587 (1989).
Packer, "The Room Where It Happens: A Skeptic's Analysis of the New Heart Failure Guidelines" J. Card. Fail. 22:726-730 (2016).
Packer, "Why is the use of digitalis withering? Another reason that we need medical heart failure specialists" Eur J Heart Failure 20:851-852 (2018).
Patel et al., "Hypotension during hospitalization for acute heart failure is independently associated with 30-day mortality: findings from ASCEND-HF" Circ Heart Failure 7:918-925 (2014).
Pellicorí et al., "IVC diameter in patients with chronic heart failure: relationships and prognostic significance" JACC Cardiovasc Imaging 6(1):16-28 (2013).
Pinz et al., "Compromised myocardial energetics in hypertrophied mouse hearts diminish the beneficial effect of overexpressing SERCA2a" J Biol Chem 286(12):10163-10168 (2011).
Revill et al., "Isaroxime" in Drugs of the Future 32(7):595-600 (2007).
Rigopoulus et al., "Acute heart failure. An unmet medical need" Herz44:53-55 (Epub Sep. 22, 2017).
Rocchetti et al., "Modulation of sarcoplasmic reticulum function by Na+/K+ pump inhibitors with different toxicity: digoxin and PST2744 [(E,Z)-3-((2-aminoethoxy)imino)androstane-6, 17-dione hydrochloride]" J Pharmacol Exp Ther 313:207-215 (2005).
Sabbah et al., "A canine model of chronic heart failure produced by multiple sequential coronary microembolizations" Am J Physiol. 260:H1379-84 (1991).
Sabbah et al., "Hemodynamic properties of a new-generation positive luso-inotropic agent for the acute treatment of advanced heart failure" Am J Cardiol. 99(2A):41A-46A (2007).
Sato et al., "Rescue of contractile parameters and myocyle hypertrophy in calsequestrin overexpressing myocardium by phospholamban ablation" J Biol Chem 276:9392-99 (2001).
Schwinger et al., "Reduced Ca(2+)-sensitivity of SERCA 2a in falling human myocardium due to reduced serin-16 phospholamban phosphorylation" J Mol Cell Cardiol. 31(3):479-91 (1999).
Seidler et al., "Cyclopiazonic acid is a specific inhibitor of the Ca2+-ATPase of sarcoplasmic reticulum" J Biol Chem. 264:17816-23 (1989).
Shah et al., "Effects of istaroxime on diastolic stiffness in acute heart failure syndromes: results from the Hemodynamic, Echocardiographic, and Neurohormonal Effects of Istaroxime, a Novel Intravenous Inotropic and Lusitropic Agent: a Randomized Controlled Trial in Patients Hospitalized with Heart Failure (HORIZON-HF) trial" Am Heart J 157:1035-41 (2009).
Shattock et al., "Na+/Ca2+ exchange and Na+/K+-ATPase in the heart" J Physiol. 15;593(6):1361-82 (2015).
Solomon et al., "Influence of nonfatal hospitalization for heart failure on subsequent mortality in patients with chronic heart failure" Circulation 116(13):1482-87 (2007).
Tamargo et al. "Investigational Positive Inotropic Agents for Acute Heart Failure" Cardiovasc. & Haematolog. Disorders-Drug Targets 9:193-205 (2009).
Teerlink et al., "Acute Treatment With Omecamtiv Mecarbil to Increase Contractility in Acute Heart Failure: The ATOMIC-AHF Study" J Am Coll Cardiol.67(12):1444-1455 (2016).
Teneggi et al., "Drugs' development in acute heart failure: what went wrong?" Heart Failure Rev 23:667-691 (2018).
ThackerayJT et al., "Sympathetic nervous dysregulation in the absence of systolic left ventricular dysfunction in a rat model of insulin resistance with hyperglycemia" Cardiovasc Diabetol. 10(75):1-13 (2011).
Toyoshima et al., "Modeling of the inhibitory interaction of phospholamban with the Ca2+ ATPase" Proc Natl Acad Sci USA 100:467-47 (2003).
Ventura-Clapier et al., "Bioenergetics of the failing heart" Biochim Biophys Acta. 1813(7):1360-72 (2011).
Voelkel et al., "Right ventricular function and failure: report of a National Heart, Lung, and Blood Institute working group on cellular and molecular mechanisms of right heart failure" Circulation 114(17):1883-91 (2006).
Whitbeck et al., "Increased mortality among patients taking digoxin—analysis from the AFFIRM study" Eur Heart J. 34(20):1481-8 (2013).
Zaza & Rocchetti, "Calcium store stability as an antiarrhythmic endpoint" Curr Pharm Des 21:1053-1061 (2015).
International Search Report and Written Opinion in International PCT Application No. PCT/US2019/060961, mailed Apr. 6, 2020.
Blair et al., "Rationale and Design of the Hemodynamic, Echocardiographic and Neurohormonal Effects of Istaroxime, a Novel Intravenous Inotropic and Lusitropic Agent: A Randomized Controlled Trial in Patients Hospitalized With Heart Failure (HORIZON-HF) Trial" Am. J. Therap. 15(3):231-240 (2008).
Database Registry, Compound Registration No. 744195-06-0 (Sep. 14, 2004).
Arici et al., "Istaroxime Metabolite PST3093 Selectively Stimulates SERCA2a and Reverses Disease-Induced Changes in Cardiac Function" The Journal of Pharmacology and Experimental Therapeutics 384:231-244 (2022).
ClinicalTrails.govarchive NCT02617446 (2017) available at https://classic.clinicaltrials.gov/ct2/history/NCT02617446?B=2&A=1&C=merged#StudyPageTop>.
EudraCT No. 2008-003531-21 "A multicenter, randomized, double-blind, placebo-controlled parallel-group phase IIb study of the safety and efficacy of istaroxime over 24 hours at three doses in acute decompensated heart failure patients" EU Clinical Register, Debiopharm S.A. https://www.clinicaltrialsregister.eu/ctr-search/trial/2008-003531-21/FR (Mar. 26, 2016).

* cited by examiner

ISTAROXIME-CONTAINING INTRAVENOUS FORMULATION FOR THE TREATMENT OF ACUTE HEART FAILURE (AHF)

CROSS REFERENCE TO RELATED APPLICATIONS

This is a continuation of U.S. application Ser. No. 17/517,530, filed Nov. 2, 2021, which is a continuation of U.S. application Ser. No. 17/233,302, filed Apr. 16, 2021, which is a continuation of PCT/US19/60961, filed Nov. 12, 2019, which claims benefit of the filing date of U.S. Provisional Application No. 62/814,149, filed Mar. 5, 2019, the entire contents of each of which are incorporated by reference herein.

FIELD OF THE INVENTION

The present invention relates to the field of pharmaceuticals, in particular to an istaroxime-containing intravenous formulation for use for the treatment of acute heart failure.

BACKGROUND OF THE INVENTION

The prevalence of heart failure (HF) is age-dependent, ranging from less than 2% of people younger than 60 years to more than 10% of people older than 75 years (Metra M, Teerlink J R, Lancet 2017; 390:1981-1995). Most patients with HF have a history of hypertension, coronary artery disease, cardiomyopathies, or valve disease, or a combination of these disorders (Metra M, Teerlink J R, Lancet 2017; 390:1981-1995). The calculated lifetime risk of developing HF is expected to increase and those with hypertension are at higher risk (Lloyd-Jones D M et al., Circulation 2002; 106:3068-3072). Patients with HF have a poor prognosis with high rates of hospital admission and mortality.

Clinical symptoms in HF are caused by a cardiac double pathological feature that consists in an inotropic abnormality, resulting in diminished systolic emptying (systolic dysfunction) and a compliance abnormality in which the ability of the ventricles to suck blood from the venous system is impaired (diastolic dysfunction), thus reducing the amount of blood available for systolic contraction, which is an impairment of left ventricle (LV) filling. Whatever the initial triggering mechanism of HF, an abnormal distribution of intracellular $Ca^{2+}$ resulting from reduced $Ca^{2+}$ uptake by the sarcoplasmic reticulum (SR), which is the main intracellular $Ca^{2+}$ store (Schwinger R H et al., J Mol Cell Cardiol. 1999; 31(3):479-91; Bers D et al., Ann N.Y. Acad Sci 2006; 1080:165-177), underlies the impaired contractility and relaxation. This abnormal $Ca^{2+}$ distribution involves the $Ca^{2+}$-ATPase of the SR membrane (SERCA2a), an ATP dependent $Ca^{2+}$ transport pump. SERCA2a activity is physiologically limited by its interaction with phospholamban (PLN) (Asahi M et al., J Biol Chem 1999; 274: 32855-32862; Toyoshima C et al., Proc Natl Acad Sci USA 2003; 100: 467-47; Bers D M., Annu Rev Physiol 2008; 70:23-49; MacLennan D H, Kranias E G., Nat Rev Mol Cell Biol 2003; 4(7): 566-577), SERCA2a restraint is normally relieved by PLN phosphorylation by protein kinase A (PKA), a signalling pathway severely depressed as a consequence of HF remodelling (Karim C B et al., J Mol Biol 2006; 358: 1032-1040; Lohse M et al., Circ Res 2003; 93:896-906; Bers D M, Physiology 2006; 21: 380-387; Mann D L, Bristow M R, Circulation 2005; 111:2837-2849). A deficiency in cardiac SERCA2a activity is widely recognized as the main cause of the reduced $Ca^{2+}$ uptake in the SR of the failing myocardium (Bers D et al., Ann N.Y. Acad Sci 2006; 1080:165-177; Bers D M, Physiology 2006; 21: 380-387; Minamisawa S et al., Cell 1999; 99: 313-322).

In addition to its consequences on myocyte contractility and relaxation, abnormal $Ca^{2+}$ distribution also facilitates cardiac arrhythmias (Zaza A & Rocchetti M, Curr Pharm Des 2015; 21:1053-1061) and, on the long term, it accelerates myocytes loss by apoptosis (Nakayama H et al., J Clin Invest 2007; 117:2431-44). Reduced SERCA2a function also increases the energy cost of contraction, because it requires a compensatory increase in $Ca^{2+}$ extrusion through the Na—Ca exchanger (NCX), which is less energy efficient (Lipskaya L et al., Expert Opin Biol Ther 2010; 10:29-41). Substantial evidence indicates that normalization of SERCA2a function restores intracellular $Ca^{2+}$ homeostasis and improves contractility and relaxation of cardiomyocytes and of the heart in situ (Byrne M J et al., Gene Therapy 2008; 15:1550-1557; Sato et al., J Biol Chem 2001; 276: 9392-99). To summarize, recovery of SERCA2a function in HF may improve cardiac relaxation and contractility while minimizing arrhythmias, myocardial oxygen consumption and myocyte death (Lipskaia L et al., Expert Opin Biol Ther. 2010; 10:29-41). In parallel to SERCA2a activation, inhibition of the Na,K-pump can further increase intracellular $Ca^{2+}$ content without inducing excessive cytosolic $Ca^{2+}$ accumulation (Shattock M J et al., J Physiol. 2015; 15; 593(6):1361-82). Therefore, the combination of Na,K-ATPase inhibition and SERCA2a stimulation may afford further positive inotropy at a reduced risk of arrhythmogenic $Ca^{2+}$ triggering events.

Current long-term therapy of HF is centred on prevention of "myocardial remodelling" and neuro-hormonal storm (p-blockers, ACE inhibitors, aldosterone antagonists), which is a chronic maladaptive response to reduced contractility, amplifies the initial damage and underlies disease evolution (Heineke J & Molkentin D, Nat Rev 2006; 7:589-600). While this approach has indisputable merit, it does not target impaired heart "contractility" and "relaxation", which are the functional derangements defining HF and responsible for its symptoms. Indeed, particularly in the advanced disease stages, such as in patients with acute heart failure (AHF), drugs that increase myocardial contractility/relaxation ("inotropic/lusitropic agents") are still widely used and crucial for the management of patients with AHF (Metra M, Teerlink J R, Lancet 2017; 390:1981-1995). These include sympathomimetic amines (dobutamine) and levosimendan, a $Ca^{2+}$-sensitizer with a strong vasodilator effect. Unfortunately, these agents act by mechanisms with potentially harmful components, such as facilitation of life-threatening arrhythmias, increased myocardial oxygen consumption and, in some patients, impairment of an already insufficient coronary blood flow due to the fall in blood pressure caused by vasodilatation (Ashkar H & Makaryus A N, Dobutamine [updated 2018 Oct. 27], In StatPearls [Internet], Treasure Island (FL): StatPearls Publishing, 218 January 2017 (available at https://www.ncbi.nlm.nih.gov/books/NBK470431/); Gong B. et al., J Cardiothorac Vasc Anesth 2015; 29:1415-25; EDITORIAL Patel P A et al., Circ Heart Failure 2014; 7:918-925). This limits the use of these agents for relieving the symptoms of the AHF, as clearly stated in both the US and EU guidelines that assign to them and evidence grade C, which is the lowest level of evidence based on the results of the available clinical trials (Rigopoulus A G et al., Herz 2017 Sep. 22; Butler J et al., EurJ Heart Fail. 2018; 20(5):839-841; Georghiade M et al., J Am Coll Cardiol. 2008; 51:2276-85). Furthermore, these agents do not improve patient's prognosis and survival, and their therapeutic use must be carefully monitored (Ashkar H & Makaryus A N, Dobutamine [updated 2018 Oct. 27], In StatPearls [Internet], Treasure Island (FL): StatPearls Publishing, 2018 January 2017 (available at https://www.ncbi.nlm.nih.gov/books/NBK470431/); Gong B. et al., J Cardiothorac Vasc Anesth 2015 29:1415-25).

Among positive inotropes, the cardiac glycoside Digoxin, which is an inhibitor of the Na,K-ATPase enzymatic activity, has been one of the most commonly prescribed medications in the past. However, its use has been decreasing over the last decades because of the difficulty in maintaining digoxin serum concentration ranges at which digoxin displays its beneficial effects (0.5-0.7 ng/ml) without reaching the threshold level of 0.9 ng/ml, above which is observed an increased risk of death due mainly to arrhythmias (Packer M, Journal of Cardiac Failure 2016; 22:726-730; Packer M, Eur J Heart Failure 2018; 20:851-852). OMECAMTIV MECARBIL, a cardiac myosin activator that increases cardiac contraction without improving the impaired relaxation, is under clinical development, but its cardiac effects are also associated with an increase of high sensitive troponin plasma levels that indicates some degree of cardiomyocytes injury/damages (Teerlink J R et al., J Am Coll Cardiol. 2016; 67(12):1444-1455).

Intensive research is also in progress for the development of HF drugs with mechanisms of action other than positive inotropy. The agents most investigated and under clinical development are: SERELAXIN—recombinant relaxin 2 mediator; ULARITIDE—recombinant natriuretic peptide; BMS986231—NO donor; ADRECIZUMAB—Adrenomedullin inhibitor; ANX-042—spliced variant of NP; TD1439—Neprylisin (NEP) inhibitor. However, when evaluated in clinical phase 2-3 trials, none of these new agents has met the primary end-point.

The clinical course and prognosis of a patient with chronic heart failure (CHF) is much worse after an episode of AHF (Solomon S D et al., Circulation 2007; 116:1482-87; Teneggi V et al., Hear Failure Rev 2018; 23:667-691). AHF can be defined as the new onset or recurrence of symptoms and signs of heart failure, requiring urgent evaluation and treatment and resulting in unscheduled care or hospital admission (Teneggi V et al., Heart Failure Rev 2018; 23:667-691; Packer M, Eur J Heart Failure 2018; 20:851-852). Half of the patients with AHF have reduced systolic function (HFrEF), representing a target for potential therapies (Braunwald E., Lancet 2015; 385:812-24). Therapies for AHF in patients with reduced ejection fraction (HFrEF) have focused on alleviating congestion with vasodilators, diuretics, or ultrafiltration or increasing cardiac output with positive inotropes. Although this therapeutic strategy has reduced the risk of sudden cardiac death, the post-discharge event rate remains unacceptably high in patients hospitalized for AHF. Many unwanted cardiovascular side effects can be caused by the available therapy, such as myocardial ischemia, cardiac injury and arrhythmias consequent to the inotrope therapy, particularly in patients with coronary artery disease (CAD) (Abraham W T et al., J Am Coll Cardiol 2005; 46:57-64; Flaherty J D et al., J Am Coll Cardiol. 2009; 53(3):254-63), hypotension and low perfusion of the peripheral organs (kidney) caused by vasodilators particularly in HF patients with low blood pressure. Accordingly, the main goal during hospitalization is to improve cardiac output without causing cardiac and/or kidney injury.

Moreover, there has been little focus on examining or treating an impaired left ventricular (LV) diastolic relaxation that, in the remaining 50% of patients with HF but preserved (50) ejection fraction (HFpEF) or mid-range (40-49) reduction ejection fraction (HFmrEF or HFmEF), is responsible for the symptoms of HF (Butler J et al., Eur J Heart Fail. 2018; 20, 839-841; Bonsu K O et al., Heart Failure Reviews 2018; 23:147-156). In addition, patients with AHF who have reduced EF also exhibit an impairment of ventricular relaxation that contributes to the overall failure of cardiac function. A variety of echocardiographic indexes has been developed to measure the cardiac relaxation capacity both in animal models and patients with HF (e.g., decreased early mitral annular tissue velocity [e'] and decreased early mitral inflow [E] deceleration time [DT]), along with echocardiographic parameters of increased LV filling pressure (e.g., E/e' ratio). Even though the correspondence of the single index changes is not perfectly superimposable in some animal models and patients, their overall changes in animal models of ventricular relaxation impairment are certainly translatable to the human condition and used to study the drug effect in AHF (Shah S A et al., Am Heart J 2009; 157:1035-41).

Various therapeutic approaches that increase SERCA2a function have been previously investigated. These include SERCA2a overexpression by gene transfer (Byrne et al., Gene Therapy 2008; 15:1550-1557) or PLN inactivation by expression of mutants with negative dominance (Hoshijima M et al., Nat. Med. 2002; 8:864-871; Iwanaga Y et al., J Clin Invest 2004; 113, 727-736), AdV-shRNA (Suckau L et al., Circulation 2009; 119:1241-1252), microRNA (Größl T et al., PLoS One 2014; 9:e92188) or antibodies (Kaye D M et al., J. Am. Coll. Cardiol. 2007; 50:253-260). As highlighted by the negative results of the largest phase 2b clinical trial applying SERCA2a gene delivery in HF (CUPID 2), these approaches suffer from major problems in construct delivery (viral vectors etc.) and dose adjustment that are far from being solved (Hulot J S, Eur Heart J 2016; 19:1534-1541). A small-molecule (pyridone derivative) attenuating the inhibitory effect of phospholamban on SERCA2a activity, which is structurally different from istaroxime, has been recently described (Kaneko M et al., Eur J Pharmacol 2017; 814:1-7), but no data on patients are available.

From the overall picture of the state of the art, and in spite of more than 30 years of trials and related publications, the treatment of patients admitted to hospital because of AHF symptoms is still largely "opinion based" rather than being "evidence based" (Rigopoulus A G et al., Herz 2017 Sep. 22; Butler J et al., Eur J Heart Fail. 2018; 20(5):839-841; Georghiade M et al., J Am Coll Cardiol. 2008; 51:2276-85). Many of the available drugs were designed with rescue and symptom relief in mind and not necessarily to target and correct any specific underlying pathophysiology/biochemical mechanism that may be responsible for the symptoms of AHF.

As a general paradigm, drugs are molecules that produce their wanted or unwanted effect by interacting with the molecules/proteins of patients. The therapeutic benefits of these drugs depend upon their selectivity in correcting the abnormalities of the protein underlying the disease symptoms over other possible effects on proteins with misappropriated or even counterbalancing activities.

The deficiency in cardiac SERCA2a activity is widely recognized as one of the most important causes of the decreased relaxation of cardiomyocytes and increased susceptibility to arrhythmias in patients with cardiac failure (Bers D et al., Ann N.Y. Acad Sci 2006; 1080:165-177; Bers D M, Physiology 2006; 21:380-387; Minamisawa S et al., Cell 1999; 99:313-322; Fernandez-Tenorio M & Niggli E., J Mol Cell Cardiol. 2018 June; 119:87-95). To this end, the potential energy starved failing heart status may further potentiate the consequences of SERCA2a deficiency (Ventura-Clapier R, Gamier A, Veksler V, Joubert F., Biochim Biophys Acta. 2011 July; 1813(7):1360-72; Pinz I et al., J Biol Chem 2011; 286(12):10163-10168). In turn, these two causes, if acknowledged, may be adequately addressed. Moreover, for more than 200 years (first evidence in literature: No Author listed, An Account of the Effects of the *Digitalis Purpurea* in Dropsy, Lond Med J. 1785; 6:55-60), *Digitalis*, which was subsequently recognized to act throughout the inhibition of the Na—K pump, has been used to increase cardiac pumping activity in spite of some unwanted side effects (e.g., arrhythmias or long term cardiomyocytes damage) (Hougen T J, Friedman W F., Am J Physiol. 1982 October; 243(4):H517-22; Whitbeck M G et al., Eur Heart J. 2013 May; 34(20):1481-8). The latter effects are very likely due to the increased cardiomyocytes cytoplasmic $Ca^{2+}$ that, on one hand is useful for stimulate contraction but, on the other, may favor the above mentioned side effect that are further enhanced by the deficiency of SERCA2a activity (Zaza A & Rocchetti M, Curr Parm Des 2015: 21:1053-1061). Consequently, drugs with a combined "selective" effect on these two molecular targets may be beneficial to patients or, at least, may prove or disprove the clinical impact of these two molecular mechanisms.

Notwithstanding the differences in the therapeutic response and outcome of subsets of patients having different degrees of deficiency in relaxation or contraction (Butler J, Eur J Heart Fail. 2018; 20, 839-841; Bonsu K O et al., Heart Failure Reviews 2018; 23:147-156) (considering the parameters HFrEF HF, HFmEF or HFpEF Heart Failure reduced Ejection Fraction (=<40), Heart Failure moderate reduction (m or mr) Ejection Fraction (between 40 and 50) Heart Failure preserved Ejection Fraction (>50)), it is mandatory to develop therapeutic strategies aimed at assessing the proper combination of the two activities on SERCA2a activation and Na—K pump inhibition for the three subsets of patients.

In particular, there is a strong and, to date, unmet need to improve the therapy of acute heart failure in HFpEF patients (Bonsu K O et al., Heart Failure Reviews 2018; 23:147-156) for whom an improvement of diastolic function by correcting the underlying molecular mechanism has not been yet achieved.

Istaroxime (PST 2744) is disclosed in EP0825197 and in De Munari S. et al., J. Med. Chem. 2003, 64, 3644-3654 and is the compound (3Z,5a)-3-[(2-aminoethoxy)imino]androstane-6,17-dione. Istaroxime is a new small-molecule drug under clinical development for the treatment of AHFS that is endowed of the double mechanism of action of inhibiting the $Na^+/K^+$ pump (Micheletti R et al., J Pharmacol Exp Ther 2002; 303:592-600) while activating SERCA2a (Rocchetti M et al., J Pharmacol Exp Ther 2005; 313:207-15).

At the same level of inotropy, the proarrhythmic effect of istaroxime is considerably lower than that of digoxin, a pure Na—K pump inhibitor (Rocchetti M et al., J Pharmacol Exp Ther. 2005; 313:207-15). This suggests that, by improving $Ca^{2+}$ clearance from the cytosol (Alemanni, J Mol Cell Cardiol 2011; 50:910-8), SERCA2a stimulation may also minimize the proarrhythmic effect of Na—K pump blockade (Rocchetti M et al., J Pharmacol Exp Ther 2005; 313:207-15; Zaza A & Rocchetti, M Curr Pharm Des 2015; 21:1053-1061) while preserving its inotropic effect. The reduction of the proarrhythmic effect by istaroxime has been confirmed in clinical studies (Georghiade M et al., J Am Coll Cardiol 2008; 51:2276-85), wherein istaroxime was administered as a continuous 6-hour infusion.

In HF patients, istaroxime infusion improved both systolic and diastolic functions. Amelioration of systolic function was detected as increases in contraction tissue velocity (s') and in the slope of end-systolic elastance (ESPVR slope); increased diastolic compliance was revealed by an increment in the early relaxation tissue velocity (e') and decreased end-diastolic elastance (EDPVR slope) (Shah S A et al., Am Heart J 2009; 157:1035-41).

According to the results described in the Horizon study by Gheorghiade (Gheorghiade M et al., J Am Coll Cardiol 2008; 51:2276-85), where istaroxime has been infused for 6 hours, the plateau effect on the improvement of diastolic relaxation, continuously measured as a decrease in PCWP (pulmonary capillary wedge pressure), occurs after 3 hours of infusion, after which the level of PCWP remains constant up to 6 hours. As it may be expected from the parallel dual targets, SERCA2a and the Na—K pump, there is no clear separation between the effects on the echocardiographic indexes of relaxation and those of contraction when increasing the infusions doses of istaroxime. Therefore, the potential beneficial effect due to the SERCA2a activation cannot be separated from the potential detrimental effect due to the Na—K pump inhibition when Istaroxime is infused up to 6 hours. Even though both the clinical (Gheorghiade M et al., J Am Coll Cardiol. 2008; 51:2276-85; Shah S A et al., Am Heart J 2009; 157:1035-41) and experimental studies in dog (Mattera G G et al., Am J Cardiol 2007; 99[suppl]:33A-40A) have demonstrated that the presence of the SERCA2a-stimulating activity of istaroxime considerably reduces the pro-arrhythmic activity associated to the Na—K pump inhibition, studies are still not satisfactory as to the clinical outcome, in particular to ensure a properly improved diastolic function and a safer discharge of the patient from hospital. As a matter of fact, the Gheorghiade and Shah clinical trials (Gheorghiade M et al., J Am Coll Cardiol 2008; 51:2276-85; Shah S A et al., Am Heart J 2009; 157:1035-41) found that, at the end of the 6 hours infusion, traditional parameters of LV systolic performance, such as stroke volume index (SVI) and Ejection fraction (EF), did not change dramatically with istaroxime compared to placebo and the duration of the effect on the diastolic relaxation was not properly discussed.

The overall HORIZON study where istaroxime has been infused for 6 hours (see Gheorghiade M et al., J Am Coll Cardiol. 2008; 51:2276-85; Shah S A et al., Am Heart J 2009; 157:1035-41) showed a greater improvement of systolic contraction than of diastolic relaxation within a dose range of 0.5 µg/Kg/min and 1.5 µg/Kg/min.

An improved diastolic function is expected to be achieved by a "pure" SERCA2a activator. However, notwithstanding the intense research on discovering small molecules or gene therapy aimed at selectively activating SERCA2a, no promising clinical outcomes have been reached so far.

Accordingly, there is a long-felt need for an advance in the treatment of acute heart failure, in particular for improving diastolic function. The present invention satisfies the above needs and overcomes the problem of prior art.

SUMMARY OF THE INVENTION

It has surprisingly been found that the intravenous infusion of istaroxime for a time longer than 6 hours and up to 48 hours or more provides unexpected improvements to the cardiac diastolic relaxation echocardiographic indexes with respect to the same infusion for 6 hours or less, while the echocardiographic indexes of systolic contraction are almost unchanged from 6 hours to 24 hours of infusion time.

Described herein are pharmaceutical compositions containing istaroxime formulated for intravenous infusion in a human subject for use in a treatment method for acute heart failure. In particular, the administration by infusion is for a duration longer than 6 hours, whereby the diastolic relaxation is improved as compared to administration of istaroxime by intravenous infusion for a duration of 6 hours or less (e.g., from 3 to 6 hours). In some embodiments, the diastolic relaxation improvement is measured by echocardiographic parameter E/A, E/e' or by pulmonary capillary wedge pressure. In some embodiments, the infusion duration is up to about 24 hours. In others, it is up to about 36 or 48 hours. In such embodiments, the pharmaceutical composition containing istaroxime is administered at a dose between 0.2 µg/kg/min and 1.5 µg/kg/min; preferably it is administered at a dose between 0.25 µg/kg/min and 1.0 µg/kg/min.

In some embodiments, the pharmaceutical composition containing istaroxime is administered for a duration sufficient to produce a plasma level of an istaroxime metabolite that is greater than about 5 ng/ml for at least about 6 hours. In particular, the istaroxime metabolites may comprise a formula (II) or a formula (III) compound, such as:

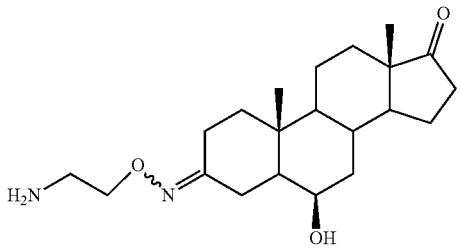

Formula (II)

PST 2915

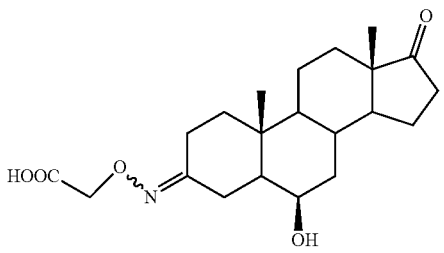

Formula (III)

PST 3093

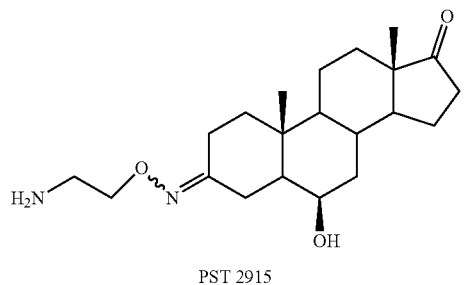

Formula (II)

PST 2915

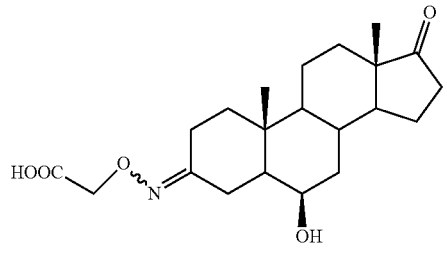

Formula (III)

PST 3093

In some embodiments, the human subject suffers from heart failure with preserved ejection fraction (HFpEF) or mid-range reduction ejection fraction (HFmEF) and/or undergoing a therapeutic treatment for heart failure with one or more further therapeutically active ingredients.

Another aspect of the invention features a compound having a formula (II) or formula (III):

In some embodiments, the compounds having the formula (II) or (III) are used in the treatment of a disease requiring the activation of SERCA2a, such as a cardiovascular disease. In particular, the compounds may be used to treat acute heart failure. In some aspects, these compounds are included in an admixture with at least one pharmaceutically acceptable vehicle and/or excipient.

Also disclosed herein are methods for treating an individual having heart failure that include the steps of (1) providing an individual having heart failure; (2) administering a therapeutically effective amount of a pharmaceutical composition containing istaroxime to the individual for an infusion duration of longer than 6 hours; and (3) measuring one or more parameters of heart function, such as diastolic relaxation. In such methods, the administering of the pharmaceutical composition results in an improvement in diastolic relaxation as compared to istaroxime administered by intravenous infusion for 6 hours or less, thereby treating the individual having acute heart failure. In preferred embodiments, the individual is human. In particular embodiments, the infusion duration is up to about 24 hours. In other embodiments, the infusion duration is up to about 36 hours. In still others, the infusion duration is up to about 48 hours. In such methods, the istaroxime may be administered at a dose of about 0.2 µg/kg/min to about 1.5 µg/kg/min. Preferably, it is administered at a dose of about 0.25 µg/kg/min to about 1.0 µg/kg/min.

In some embodiments, the individual is diagnosed with heart failure with preserved ejection fraction (HFpEF) or mid-range reduction ejection fraction (HFmEF). In other embodiments, the individual is undergoing a therapeutic treatment for heart failure with one or more further therapeutically active ingredients.

Also featured herein are pharmaceutical compositions containing istaroxime for intravenous infusion in an individual for the treatment of acute heart failure. In such aspects, the administration is for an infusion duration sufficient to produce in the individual a plasma concentration level of an istaroxime metabolite that is greater than about 5 ng/ml for an accumulation period of at least about 6 hours, whereby the diastolic relaxation is improved as compared to administration of istaroxime prior to the accumulation period. Preferably, the istaroxime metabolite comprises formula (II) or (III).

In some embodiments, the infusion duration is sufficient to produce a plasma concentration level of istaroxime metabolite that is greater than about 10 ng/ml for an accumulation period of at least about 6 hours. In other embodiments, the plasma concentration level of the istaroxime metabolite is greater than about 15 ng/ml for an accumulation period of at least about 6 hours. In still others, it is greater than about 20 ng/ml. In some embodiments, the compositions are administered at a dose of about 0.2 µg/kg/min to about 1.5 µg/kg/min; preferably from about 0.25 µg/kg/min to about 1.0 µg/kg/min).

Other aspects of the invention feature methods for treating an individual having heart failure, including the steps of: (1) providing an individual having heart failure; (2) administering a therapeutically effective amount of a pharmaceutical composition containing istaroxime to the individual for an infusion duration sufficient to produce a plasma concentration level of an istaroxime metabolite that is greater than about 5 ng/ml for an accumulation period of at least about 6 hours; and (3) measuring one or more parameters of heart function, wherein the one or more parameters of heart function comprises diastolic relaxation.

In some embodiments, the plasma concentration level of the istaroxime metabolite is greater than about 10 ng/ml for an accumulation period of at least about 6 hours. In other embodiments, it is greater than about 15 ng/ml for an accumulation period of at least about 6 hours. In still others, it is greater than about 20 ng/ml for an accumulation period of at least about 6 hours. The therapeutically effective does of the composition is between about 0.2 µg/kg/min and about 1.5 µg/kg/min; preferably, between 0.25 µg/kg/min and 1.0 µg/kg/min.

In yet another aspect of the invention, a method for treating an individual having acute heart failure is featured that includes the steps of (1) providing an individual having acute heart failure; (2) measuring one or more parameters of heart function, wherein the one or more parameters of heart function comprises diastolic relaxation as measured by echocardiographic parameter E/A, E/e' or by pulmonary capillary wedge pressure; and (3) administering a therapeutically effective amount of a pharmaceutical composition containing istaroxime to the individual at a dose of at least about 1.0 µg/kg/min for a duration sufficient to improve diastolic relaxation in the individual. Then, after improvement of diastolic relaxation in the individual, a therapeutically effective amount of a second pharmaceutical composition containing istaroxime is administered to the individual at a dose of between about 0.25 µg/kg/min to about 1.0 µg/kg/min for an infusion duration sufficient to produce in the individual a plasma concentration level of an istaroxime metabolite that is greater than about 5 ng/ml for an accumulation period of at least about 6 hours. In such aspects, the istaroxime metabolite comprises formula (II) or (III).

Still other aspects of the invention feature methods for treating an individual having heart failure that include (1) providing an individual having heart failure; (2) administering a therapeutically effective amount of a pharmaceutical composition containing an istaroxime metabolite to the individual for an infusion duration of longer than 6 hours; and (3) measuring one or more parameters of heart function, such as diastolic relaxation. In some aspects, the infusion duration is between 6 hours and 48 hours at a dose of between about 0.2 µg/kg/min to about 1.5 µg/kg/min; preferably between about 0.25 µg/kg/min to about 1.0 µg/kg/min. In a particular embodiment, the individual is diagnosed with heart failure with preserved ejection fraction (HFpEF) or mid-range reduction ejection fraction (HFmEF).

BRIEF DESCRIPTION OF THE DRAWINGS

These and other features and advantages of the present disclosure will become better understood with regard to the following description, appended claims, and accompanying drawings wherein:

DETAILED DESCRIPTION OF THE INVENTION

Figure 1:
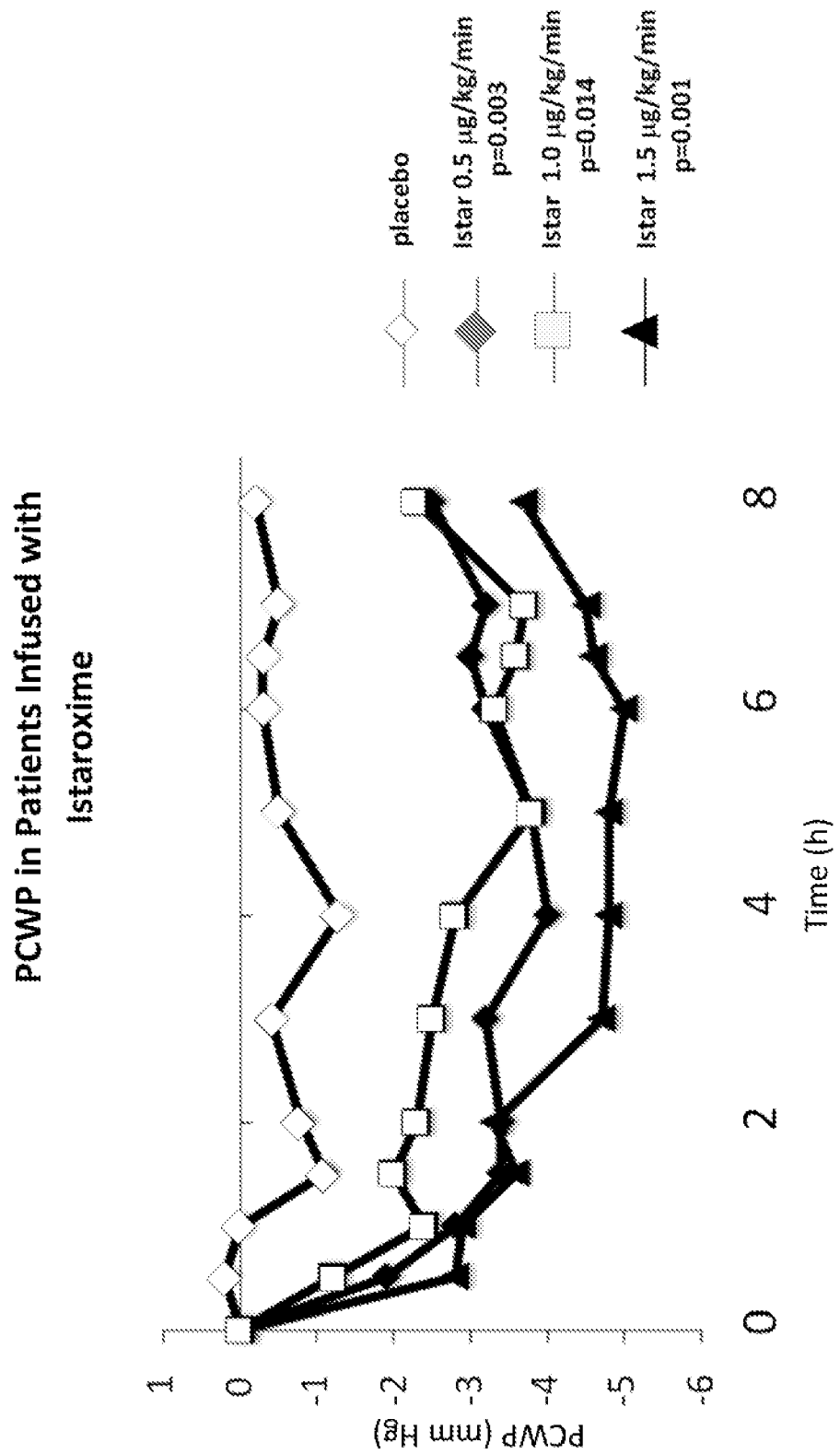
FIG. 1 shows a time course of changes in pulmonary capillary wedge pressure (PCWP) in patients infused with placebo (white diamond) as compared to istaroxime infusion for 6 hours at a dose of 0.5 µg/kg/min (dark diamond), 1.0 µg/kg/min (square), and 1.5 µg/kg/min (triangle). The X-axis represents the average PCWP (mmHg), and the Y-axis represents time (hours).

The compositions and methods disclosed herein confer to individuals suffering from heart failure unexpected benefits. Provided herein are compositions comprising istaroxime or a metabolite thereof. Further, as disclosed herein, infusion with istaroxime or its metabolites for more than 6 hours improves selectively cardiac relaxation over cardiac contraction. Moreover, istaroxime infusion time can be extended to allow for the accumulation of one or more of its metabolites, at least one of which exhibits single-function SERCA2a activation (i.e., behaves as a "pure" SERCA2a activator). The compositions and methods disclosed herein will be described in more detail below.

Definitions

Unless defined otherwise, all technical and scientific terms used herein have the same meaning as those commonly understood by one of ordinary skill in the art to which this invention belongs. Standard techniques are used unless otherwise specified. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

As used herein, the singular forms "a," "an," and "the" include the plural referents unless the context clearly indicates otherwise.

The term "about" refers to the variation in the numerical value of a measurement, e.g., volume, time, pressure, concentration, etc., due to typical error rates of the device used to obtain that measure. In one embodiment, the term "about" means within 5% of the reported numerical value, preferably, the term "about" means within 3% of the reported numerical value.

The term "heart failure" refers to a clinical syndrome characterized by typical symptoms (e.g., breathlessness, ankle swelling and fatigue) that may be accompanied by signs (e.g., elevated jugular venous pressure, pulmonary crackles and peripheral edema) caused by a structural and/or functional cardiac abnormality, resulting in a reduced cardiac output and/or elevated intracardiac pressures at rest or during stress.

The terms "acute heart failure" or "AHF" are used interchangeably herein and refer generally to a rapid onset or worsening of symptoms and/or signs of HF requiring immediate treatment and hospitalization. The current definition of "acute heart failure" is rather nonspecific and may include a broad spectrum of conditions with several phenotypes characterized by different clinical presentation, etiology, precipitating factors, therapeutic approach, and prognosis. In addition, a large proportion of patients have a subacute course of the disease with a progressive worsening of signs and symptoms of HF which could develop days before hospital admission.

The terms "chronic heart failure" or "CHF" are used interchangeably herein and refer to the current clinical classification of chronic HF based on the presence of signs and symptoms of HF and left ventricular ejection fraction (LVEF), recognizing three categories: "heart failure with reduced ejection fraction" or "HFrEF," which is characterized by an LVEF of less than about 40%; "heart failure with mid-range ejection fraction" or "HFmEF" or "HFmrEF," which is characterized by an LVEF from about 40% to about 49%; and "heart failure with preserved ejection fraction" or "HFpEF," which is characterized by an LVEF of equal to or greater than about 50%. The terms "HFmrEF" and "HFpEF" include two additional criteria, namely increased natriuretic peptides levels (BNP>35 μg/ml and/or NT-proBNP>125 μg/mL) associated with the evidence of structural and/or functional heart disease (left ventricular hypertrophy and/or left atrium enlargement and/or evidence of diastolic dysfunction). The efficacy of HF evidence-based medications have been confirmed only in patients with "HFrEF," whereas no treatment demonstrated a significant improvement of outcomes in patients with "HfpEF".

The term "treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by an individual, such as a human patient.

The term "preventing" refers to the prevention of the disease or condition, e.g., acute heart failure, in an individual, such as a human patient. For example, if an individual at risk of developing heart failure is treated with the methods of the present invention and does not later develop heart failure, then the disease has been prevented in that individual.

The term "treat or prevent" is sometimes used herein to refer to a method that results in some level of treatment or amelioration of the disease or condition, and contemplates a range of results directed to that end, including but not restricted to prevention of the condition entirely.

As used herein, the term "pharmaceutically acceptable carrier" means a chemical composition with which an istaroxime compound or a metabolite of istaroxime may be combined and which, following the combination, can be used to administer the compound to a mammal.

As used herein, the term "pharmaceutically acceptable" salt, solvate, hydrate, or ester means a salt, solvate, hydrate, or ester form of the active ingredient which is compatible with any other ingredients of the pharmaceutical composition, which is not deleterious to the subject to which the composition is to be administered.

The term "intravenous infusion" refers to the administration or delivery of liquid substances directly into a vein of a mammal. Typical "infusions" use only the pressure supplied by gravity.

The term "parameter" as used herein to refer to measuring heart function means any heart function that is observable or measurable using suitable measuring techniques available in the art. A non-limiting list of exemplary "parameters" of heart function include heart rate, blood pressure, diastolic relaxation, systolic contraction, LVEF, diastolic blood pressure, systolic blood pressure, cardiac output, stroke volume, deceleration slope, cardiac index, mitral inflow velocity, and the like. As one having ordinary skill in the art will appreciate, measuring one or more "parameters" of heart function can be used to detect heart dysfunction as compared to the average normal parameters and can also be used to determine whether heart function has improved following or during treatment.

The terms "therapeutically active" or "active" ingredient or compound refer to a substance that provides a beneficial effect to the individual to whom the substance is administered. A "therapeutically effective amount" or "therapeutically effective dose" is the amount of a composition or active ingredient sufficient to provide a beneficial effect to the individual to whom the composition or active ingredient is administered.

Description

The present invention is based on the unexpected discovery that istaroxime infusion for more than 6 hours provides a prevailing lusitropic effect or improvement of the reduced cardiac relaxation, as shown by the clear changes of the echo indexes of cardiac relaxation (E/A DTs, e', E/e' and left atrial area or volume) while those of contraction (Sa and s) remained unchanged. In some embodiments, the istaroxime infusion is between about 6 hours and up to 48 hours or more, e.g., 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 31 h, 32 h, 33 h, 34 h, 35 h, 36 h, 37 h, 38 h, 39 h, 40 h, 41 h, 42 h, 43 h, 44 h, 45 h, 46 h, 47 h, 48 h, or more. For instance, the infusion can be for up to 24 hours, or up to 36 hours, or up to 48 hours, or more. In other embodiments, the duration of the infusion is greater than 6 hours and equal to or less than about 48 hours, or greater than 6 hours and equal to or less than about 36 hours, or greater than 6 hours and equal to or less than about 24 hours, or greater than 6 hours and equal to or less than about 12 hours. It being understood that the infusion or istaroxime or a metabolite thereof provides a prevailing lusitropic effect or improvement of the reduced cardiac relaxation as compared to infusion with istaroxime or a metabolite thereof for a period of 6 hours or less, e.g., 0, 1, 2, 3, 5, or 6 hours.

Figure 2A:
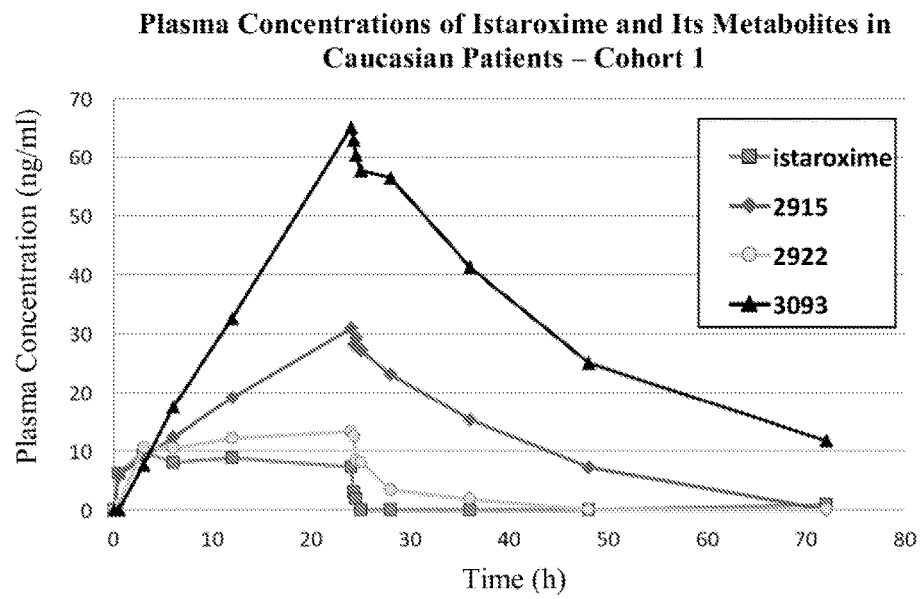
FIG. 2A shows the plasma levels of istaroxime (square) and its metabolites in Caucasian patients intravenously infused with 0.5 µg/kg/min istaroxime for 24 hours. The metabolites are PST 2915 (diamond), PST 2922 (circle), and PST 3093 (triangle). The X-axis represents the plasma concentration (ng/ml), and the Y-axis represents time (hours).
Figure 2B:
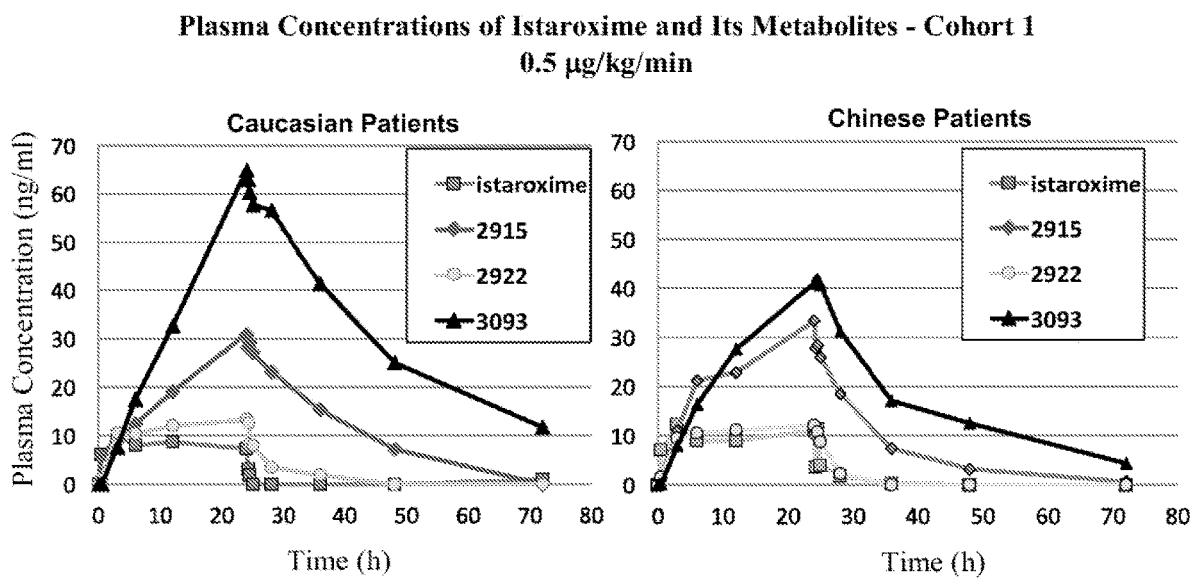
FIG. 2B shows the plasma levels of istaroxime (square) and its metabolites in Caucasian patients (left panel) and Chinese patients (right panel) intravenously infused with 0.5 µg/kg/min istaroxime for 24 hours. The metabolites are PST 2915 (diamond), PST 2922 (circle), and PST 3093 (triangle). The X-axis represents the plasma concentration (ng/ml), and the Y-axis represents time (hours).
Figure 2C:
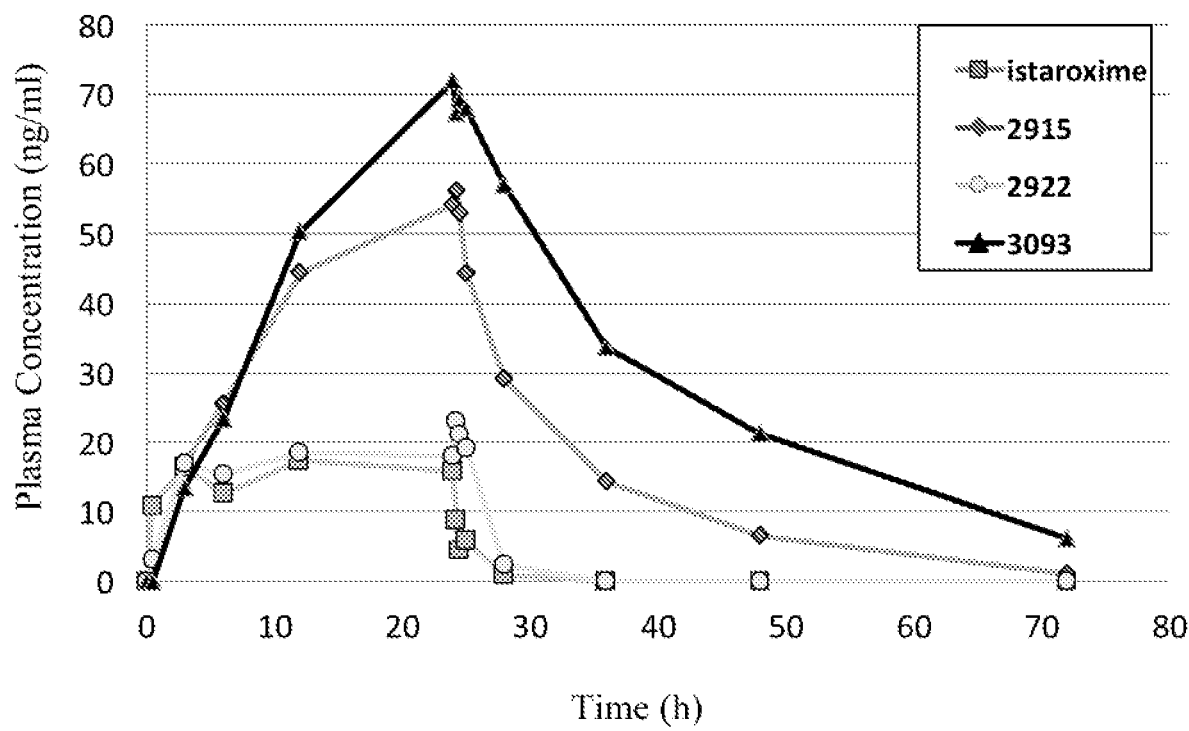
FIG. 2C shows the plasma levels of istaroxime (square) and its metabolites in Chinese patients intravenously infused with 1.0 µg/kg/min istaroxime for 24 hours. The metabolites are PST 2915 (diamond), PST 2922 (circle), and PST 3093 (triangle). The X-axis represents the plasma concentration (ng/ml), and the Y-axis represents time (hours).

Importantly, an analysis of four independent groups of data confirms that istaroxime infusion for more than 6 hours provides a prevailing lusitropic effect and improvement of the cardiac relaxation. First, FIG. 1 shows a PCWP time course of patients intravenously infused with istaroxime for up to 6 hours. As previously described in the HORIZON study of patients intravenously infused with istaroxime for 6 hours, time course changes of PCWP, which the skilled artisan will appreciate as a valid marker of diastolic relaxation, shows an improvement of diastolic relaxation during the initial 3 hours, but then the average PCWP plateaus and remains unchanged for the following 3 hours (see FIG. 1). In other words, patients infused for 6 hours with istaroxime showed no improvement in diastolic relaxation between 3 and 6 hours of the infusion. In contrast, patients administered intravenous infusion of istaroxime for 24 hours exhibit a clear increase in echocardiographic indexes of diastolic relaxation from 6 to 24 hours, while the indexes of systolic contraction remain unchanged (see Tables 1A-1C). Moreover, as shown in FIGS. 2A-2C, there is a progressive and remarkable increase in the plasma concentration of the istaroxime metabolite PST 3093 at the 6-hour and 24-hour time points, while the plasma concentration of istaroxime remains constant throughout this time interval. Finally, the synthesis of PST 3093 and the subsequent biochemical and pharmacological studies demonstrate that this compound is endowed of a selective SERCA2a stimulatory activity (see, e.g., Example 2 and Table 3) at concentrations well below the that of the intravenous infusion studies shown in FIG. 2. Moreover, its infusion in a rat model of diabetic cardiomyopathy is associated with an improvement in diastolic relaxation (see Table 5). According to Munafò et al. (Nature 2018, 553(7689):399-401), simply repeating single experiments is not sufficient, but rather many lines of evidence is needed. Thus, it is the consistency among these four independent findings that, per se, confers scientific robustness to the assertion that istaroxime infusion for more than 6 hours provides a prevailing lusitropic effect and improvement of the cardiac relaxation as compared to shorter infusion times.

These findings are entirely unexpected, since the plasmatic level of istaroxime remains constant (i.e., within about 10 ng/ml at 3 hour time point to about 8 ng/ml) during the following time points for the whole duration of the infusion. The present inventors have discovered that in humans this prolonged infusion of istaroxime generates an increasing concentrations of istaroxime metabolites PST 3093 and PST 2915, which behave as selective or "pure" SERCA2a activator. Further, this selectively is even greater for PST 3093, thus explaining the unexpected effect in improving diastolic function over systolic function.

Consequently, patients with HFpEF or HFmEF may benefit from a more selective correction of the impaired diastolic relaxation by increasing the plasma level of the metabolite over that of istaroxime. Thus, minimizing the $Na^+/K^+$ pump inhibition, notwithstanding the constant plasma level of istaroxime, with its associated unwanted effects in term of arrhythmias or cardiomyocytes damage. Advantageously, the clinical outcome is a safer patient discharge after treatment of acute heart failure.

Istaroxime is an inotropic compound having the following structural formula (I):

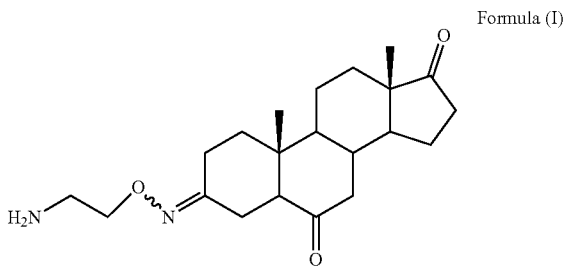 [SMILES: C[C@]12CCC(=NOCCN)CC1C(=O)CC1C2CC[C@]2(C)C(=O)CCC12]

Formula (I)

Upon administering to a mammal, such as a human, istaroxime is metabolized into several metabolites that are capable of activating SERCA2a.

Istaroxime metabolic pathway is illustrated below:

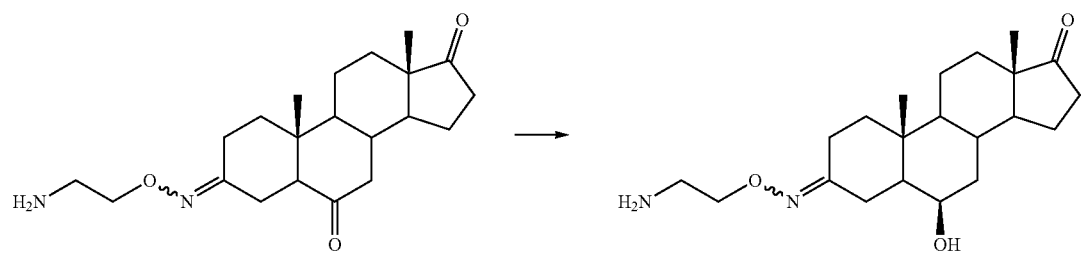

Istaroxime - PST 2744          PST 2915

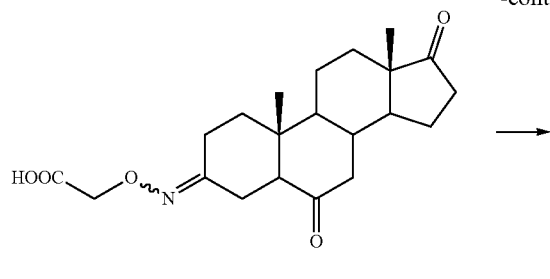

PST 2922 → PST 3093

As such, disclosed herein are metabolites of istaroxime having SERCA2a activity that have the following structural formulas (II) and (III):

Formula (II)

PST 2915

Formula (III)

PST 3093

In preferred embodiments, the metabolite of istaroxime (here also named PST 3093) endowed with selective or "pure" SERCA2a activity is the compound of formula (III).

The present inventors have isolated and characterized PST 2915 and PST 3093. In rats with diabetic cardiomyopathy, administration of PST 3093 showed improved diastolic relaxation and overall cardiac function as measured as an increase of stroke volume SV.

Therefore, it is also an object of the present invention to utilize the SERCA2a-activation properties of the compound of formula (II) or the compound of formula (III), or their respective pharmaceutically acceptable salts or esters, as well as their different hydrates, solvates, polymorphic forms. Another object of the present invention is the compound of formula (II) or formula (III) for use as medicament, in particular for treating diseases requiring the activation of SERCA2a, more preferably for the treatment of heart failure or acute heart failure.

Also disclosed herein is a pharmaceutical composition comprising the compound of formula (II) or formula (III), in an admixture with at least one pharmaceutically acceptable vehicle and/or excipient. In preferred embodiments, the pharmaceutical composition is formulated for administering to an individual by infusion, preferably, it is by intravenous infusion.

The surprising effect of the present invention on the improved cardiac diastolic relaxation can be better appreciated from the comparison of cardiac parameters between the 6-hour infusion of the previous study (HORIZON clinical trial) and the 24-hour infusion according to the present invention. The outline of the study is described below and the data at 6 hours of infusion, 24 hours of infusion, and 48 hours of infusion are summarized in Tables 1A, 15, and 1C, respectively.

The synopsis of the clinical trial is described herein:

| | |
|---|---|
| Title | The clinical study of the safety and efficacy of Istaroxime in Treatment of Acute Decompensated Heart Failure - A multicenter, randomized, double-blind, placebo controlled, parallel group clinical study. |
| Indication | Acute Decompensated Heart Failure (ADHF) |
| Objective | To Assess the safety, tolerability and efficacy of two different doses of istaroxime (0.5 and 1.0 µg/kg/min), a new agent with lusitropic and inotropic activities that improves the cardiac contraction-relaxation cycle. The 2 doses of istaroxime (0.5 and 1.0 µg/kg/min) will be infused i.v. for 24 hours in comparison with placebo, in treatment of Chinese and Caucasian patients with Acute Decompensated Heart Failure. In all the Caucasian patients and in a subset of Chinese patients pharmacokinetics and metabolism of istaroxime shall also be studied. |
| Study Design | A multicenter, randomized, double-blind, placebo-controlled, parallel group study. |
| Study Period | This study includes a screening period (Days −1), a treatment period (Day 1), a post-treatment period (Days 2-4), and a follow-up period (which includes one patient visit on Day 30). |

| | |
|---|---|
| Subject Selection Criteria | Inclusion criteria<br>Patients who fulfill the following inclusion criteria at screening will be considered for the study:<br>1. Signed informed consent;<br>2. Male or female patients 18-85 years (inclusive);<br>3. Admission for a recurrent ADHF episode with dyspnea at rest or minimal exertion and need of intravenous diuretic therapy (≥40 mg iv. furosemide);<br>4. Systolic blood pressure between 90 and 125 mmHg (limits included) without signs or symptoms of hypoperfusion including cardiogenic shock, cold extremities and peripheral vasoconstriction, oliguria/anuria, signs of cerebral hypo perfusion such as confusion;<br>5. Left ventricular (LV) Ejection fraction (EF) ≤40% measured by 2D-Echocardiography<br>6. E/Ea ratio >10<br>7. BNP ≥350 pg/mL or NT-pro-BNP ≥1400 pg/mL<br>8. Adequate echocardiography window (defined as visualization of at least 13/16 segment of the left ventricle);<br>Exclusion Criteria<br>Any of the following criteria established at screening would render a patient ineligible for the study:<br>1. Pregnant or breast-feeding women (women of child bearing potential must have the results of a negative pregnancy test recorded prior to study drug administration)<br>2. Current (within 12 hours prior to screening) or planned (through the completion of study drug infusion) treatment with any iv. therapies, including vasodilators (including nitrates or nesiritide), positive inotropic agents and vasopressors<br>3. Current or need of mechanical support (intra-aortic balloon pump, endotracheal intubation, mechanical ventilation, or any ventricular assist device),<br>4. Ongoing treatment with oral digoxin. Patient treated with digoxin cannot be randomized. However, if digoxin treatment has been stopped during the last week before randomization and the digoxin plasma level is <0.5 ng/ml, patient may be randomized;<br>5. History of hypersensitivity to the study medication or any related medication<br>6. Diagnosis of cardiogenic shock within the past month;<br>7. Acute coronary syndrome or stroke within the past 3 months;<br>8. Coronary artery bypass graft or percutaneous coronary intervention within the past month or planned in the next month;<br>9. Primary hypertrophic or restrictive cardiomyopathy or systemic illness known to be associated with infiltrative heart disease;<br>10. Cor pulmonale or other causes of right-sided HF not related to left ventricular dysfunction;<br>11. Pericardial constriction or active pericarditis;<br>12. Atrial fibrillation with marked irregularities of heart rhythm;<br>13. Life threatening ventricular arrhythmia or ICD (implantable cardioverter defibrillator) shock within the past month;<br>14. CRT (cardiac resynchronization therapy), ICD or pacemaker implantation within the past month;<br>15. Valvular disease as primary cause of HF;<br>16. Heart rate >120 bpm or <50 bpm<br>17. Acute respiratory distress syndrome or ongoing sepsis;<br>18. Fever >38°<br>19. History of bronchial asthma or porphyria;<br>20. Donation or loss of blood equal to or exceeding 500 mL, during the 8 weeks before administration of study medication;<br>21. Positive testing for Hepatitis B and/or Hepatitis C with abnormal liver functions;<br>22. Participation in another interventional study within the past 30 days;<br>23. The following laboratory exclusion criteria, verified based on results obtained within the last 24 hours of hospitalization:<br>a. Serum creatinine >3.0 mg/dl (>265 μmol/L);<br>b. Aspartate aminotransferase (ASAT) or alanine aminotransferase (ALAT) >3 × upper limit of normal,<br>c. Hemoglobin (Hb) <10 g/dL,<br>d. Platelet count <100,000/μL,<br>e. Serum potassium >5.3 mmol/L or <3.8 mmol/L, |
| Study Drugs | Test drug: Istaroxime (10 mg per vial) |
| Mode administration | Intravenous infusion via a syringe pump. |
| Treatment duration | Treatment by i.v. infusion will last 24 hours. |
| Dosing scheme | Istaroxime 0.5-1.0 μg/kg/min since the beginning. A continuous i.v. infusion for 24 hours not exceeding 144 mg for 24 hours of istaroxime for patients with body weight >100 kg shall be carried out. |

| | |
|---|---|
| Sample Size | 120 total patients (96 Chinese patients and 24 Caucasian patients) |
| Study Procedures | Screening period (between Hours −24 to −1)<br>Within a maximum of 24 hours before administration of study medication (istaroxime), a medical screening will be performed on all prospective patients to assess suitability for the study. Prior to conducting any study specific procedures, the investigator or his/her designee will explain the study fully to the patient and provide him/her with a copy of the Patient Information Sheet and Informed Consent Document. If the patient is willing to participate in the study, s/he and the investigator or his/her designee will both sign the Informed Consent Document and a copy of the signed document will be kept by the patient.<br>Treatment period (Day 1)<br>1) Confirm eligibility;<br>2) Randomization of patients (after eligibility has been confirmed)<br>3) Insertion of multiple lumen intravenous catheter<br>4) Start istaroxime or placebo infusion (date and time of infusion start must be recorded in the CRF)<br>5) cTnT (at pre-dose: two samples, then at 3 and 6, 12, 24, 48 and 72 hours after start of infusion)<br>6) NT pro-BNP at baseline and at the end of 24 hours infusion<br>7) Blood samples collection for metabolites and PK (at pre-dose, 0.5-3-6-12-24 after start of infusion and at 0.25, 0.5, 1, 4 12, 24 hours after the end of infusion) in all the Italian patients and in a subset of Chinese patients pharmacokinetics and metabolism of istaroxime shall also be studied.<br>8) Vital signs (including body temperature and dyspnoea at pre-dose, 3, 6, 12 and 24 after the start of infusion)<br>9) 12-lead ECG profile<br>10) Stop Day −1 Holter<br>11) Start 24-hour Holter ECG (Day 1 recording; to be started immediately before initiation of the study drug infusion)<br>12) Echocardiography at baseline and 6 and 24 hours after infusion start<br>13) 24-hours urine collections for measurement of istaroxime and its metabolites and urinary creatinine for the calculation of the creatinine clearance;<br>14) Blood collection for K+ and eGFR between 23 hours and 30 minutes and 23 hours and 55 minutes since infusion start;<br>15) Concomitant medication monitoring (including chronic medication; dose, date and time must be recorded on CRF)<br>16) Adverse events monitoring<br>Post-treatment period (Day 2 to Day 4)<br>Evaluations at 24 hours (day 2) from randomization include:<br>1) Vital signs (including body temperature and dyspnea);<br>2) 12-lead ECG (single ECGs);<br>3) Stop 24-hour Holter ECG;<br>4) Start 24-hour Holter ECG (Day 2 recording);<br>5) Stop istaroxime infusion (date and time of infusion end must be recorded in the CRF);<br>6) Serum potassium level and 24-hour urine collection for measurement of istaroxime metabolites and urinary creatinine for calculation of the creatinine clearance;<br>7) Serum creatinine clearance and calculation of eGFR;<br>8) cTnT (50% or 20% relative increase over the basal cTnT levels, respectively for patients with cTnT basal levels < or > of the 99% URL (upper reference levels, as defined for the Roche hs test, in patients with normal renal function, eGFR ≥85 ml/min); in patients with eGFR below this value, the renal function variations must be considered in evaluating the significance of the cTnT changes);<br>9) NT pro-BNP;<br>10) Metabolites;<br>11) Echocardiography;<br>12) Concomitant medication monitoring (including chronic medication must be recorded in the CRF);<br>13) Adverse Events monitoring.<br>Evaluations at 48 hours (day 3) include:<br>1) Vital signs (including body temperature and dyspnea);<br>2) 12-Lead ECG (single ECGs);<br>3) Stop 24-hour Holter ECG;<br>4) Standard hematology;<br>5) Standard blood chemistry;<br>6) Serum potassium level;<br>7) 24-h urine collection for measurement of istaroxime metabolites and urinary creatinine for the calculation of creatinine clearance;<br>8) Calculation of eGFR;<br>9) NT-proBNP;<br>10) cTnT;<br>11) Blood samples for istaroxime metabolites;<br>12) Echocardiography<br>13) Adverse events monitoring; |

|  |  |
|---|---|
|  | 14) Concomitant medication monitoring (including chronic medication must be recorded in the CRF);<br>Evaluations at 72 hours (day 4) include:<br>1) cTnT and NTproBNP (at 72 hours after start of infusion)<br>2) Vital signs (including body temperature and dyspnoea)<br>3) Physical examination (HF signs included)<br>4) 12-lead ECG<br>5) Adverse events monitoring<br>6) Concomitant medication monitoring (including chronic medication)<br>7) Istaroxime metabolites<br>8) Serum potassium and creatinine levels for calculation of eGFR<br>9) Creatinine clearance<br>Follow-up period and visit (Day 5 to Day 30)<br>During the follow-up period the Investigator/designee will make every effort to establish patient outcomes.<br>Evaluations on Day 30 (follow-up visit) include:<br>1) Vital signs (including body temperature and dyspnoea);<br>2) 12-lead ECG in triplicate;<br>3) Calculation of eGFR;<br>4) Standard hematology;<br>5) Standard blood chemistry;<br>6) NT-proBNP<br>7) cTnT;<br>8) Urine pregnancy test (β-HCG) for females of childbearing potential<br>9) Urinalysis;<br>10) Physical examination (HF signs included);<br>11) Adverse events monitoring;<br>12) Concomitant medication monitoring (including chronic medication) |
| Efficacy Parameters | Efficacy endpoints<br>1. Primary efficacy end-point:<br>Change from baseline to 24 hours after infusion start (treatment period Day 1) in the E/Ea ratio assessed by tissue Doppler.<br>2. Secondary efficacy end-points:<br>Change from baseline to 24 hours in the treatment period Day 1 (addressing the differences between the changes at 6 and 24 hours from baseline) of the following Echo-Doppler parameters:<br>LV Ejection fraction (EF)<br>LV end systolic and end diastolic volumes<br>Stroke volume index (SVI)<br>E, A and E/A ratio<br>Difference between the changes at 6 and 24 hours from baseline of the Tissue Doppler parameter E/Ea<br>Others Tissue Doppler parameters such as Sa, Da and Aa<br>Changes in dyspnoea assessed at 3, 6, 12, 24, 48 hours after infusion start by Visual Analog Scale (VAS) (including only patients presenting dyspnoea at baseline);<br>Area under the curve (AUC) on changes in dyspnoea assessed at 3, 6, 12, 24, 48 hours after infusion start by VAS (including only patients presenting dyspnea at baseline);<br>Changes in BNP from baseline at 24 hours;<br>Proportion of patients with hospital readmissions or emergency visits for cardiovascular reasons by Day 30;<br>Proportion of patients with episodes of worsening HF defined by the need to increase the dose or reinitiate i.v. therapy with diuretics and/or other inotropic agents during the hospitalization;<br>Length of the hospitalization; |
| Safety Parameters | Safety endpoints:<br>The following safety endpoints will be assessed during treatment and the post-treatment/follow-up periods:<br>Incidence of adverse events;<br>Change in vital signs (including body temperature and dyspnoea);<br>Change in 12-lead ECG parameters;<br>Incidence of clinically or hemodynamically significant episodes of supraventricular or ventricular arrhythmias detected by continuous ECG dynamic monitoring;<br>Change in laboratory parameters (hematology, blood chemistry and urinalysis);<br>Change in renal function;<br>Change in in cTnT;<br>Incidence of cTnT elevation (>50% or >20% relative increase over the basal cTnT levels at baseline, for patients with cTnT levels at baseline < or ≥ of the 99% URL (upper reference levels, as defined for the Roche hs test, in patients with normal renal function, eGFR ≥85 ml/min); in patients with eGFR below this value, the renal function variations must be considered in evaluating the significance of the cTnT changes);<br>Mortality at Day 30; |

| | |
|---|---|
| PK parameters | Full plasma and urine PK profile:<br>The following PK metrics will be computed for E and Z isomers (when applicable) of istaroxime plasma concentrations using non-compartmental analysis: Cmax, tmax, AUC0-t, AUC0-∞, □z, t½, CIT, MRT, Vss, Vz;<br>the following PK metrics will be computed for E and Z isomers (when applicable) of istaroxime urine concentrations: Ae, Ae %, CIR;<br>In addition, the following PK metrics will be computed as above for plasma and urine concentrations of the E and Z isomers (when applicable) of istaroxime metabolites 2915, 2922, and 3093: Cmax, tmax, AUC0-t, AUC0-∞, □z, t½ and, if possible, Ae and Ae %; |
| Statistical Analysis | Primary efficacy endpoint:<br>The primary efficacy endpoint (change from baseline in E/Ea ratio) will be analyzed using a linear mixed model for repeated measures including treatment, centre, timepoint, gender, baseline cTnT (normal <URL, abnormal ≥URL), atrial fibrillation (Yes/No) and treatment*timepoint interaction as fixed effects and baseline and baseline*timepoint interaction as covariates.<br>The primary comparison will be 0.5 µg/kg/min dose of istaroxime versus placebo at 24 hours. Highest dose of istaroxime (1.0 µg/kg/min) versus placebo will be tested as a secondary comparison.<br>Additional analyses separated by cohort will be implemented for sensitivity purpose.<br>Secondary efficacy endpoints<br>The following secondary endpoints:<br>Change from baseline to 24 hours (addressing the differences between the changes at 6 and 24 hours from baseline) of the following Echo-Doppler parameters:<br>LV Ejection fraction (EF)<br>LV end systolic and end diastolic volumes<br>Stroke volume index (SVI)<br>E, A and E/A ratio<br>Change from baseline to 24 hours in the E/Ea ratio assessed by tissue Doppler (difference between the changes at 6 and 24 hours from baseline)<br>Others Tissue Doppler parameters such as Sa, Da and Aa<br>Changes in dyspnoea using VAS score will be analysed using a mixed model for repeated measures similar to the one used for the primary efficacy endpoint.<br>AUC on changes in dyspnoea by VAS and changes in BNP will be analyzed using an ANCOVA model with treatment, centre, gender, baseline cTnT (normal <URL, abnormal ≥URL) and atrial fibrillation (Yes/No) as fixed effects and baseline dyspnea as covariate.<br>Number and proportion of patients with:<br>hospital readmissions or emergency visits for cardiovascular reasons within Day 30<br>episodes of worsening HF defined by the need to increase the dose or reinitiate i.v. therapy with diuretics and/or other inotropic agents during the hospitalization<br>will be summarized by treatment groups using descriptive statistics.<br>Length of hospitalization will be summarized by treatment group using descriptive statistics.<br>Safety endpoints<br>The number and the percentage of patients experiencing adverse events, adverse drug reactions, serious adverse events and adverse events leading to study withdrawal will be summarized by treatment group.<br>Adverse events will also be summarized by treatment group by means of System Organ Class and Preferred Term using the MedDRA dictionary.<br>Vital signs (including body temperature and dyspnoea), 12-lead ECG parameters, incidence of clinically or hemodynamically significant episodes of supraventricular or ventricular arrhythmias, laboratory parameters, renal function, cTNT, increase of cTNT and mortality will be summarized by treatment group using descriptive statistics. |

Echocardiography was performed on patients according to international standards (see, for example, Lang R M et al., J Am Soc Echocardiogr 2005; 18(12):1440-63; Nagueh S F et al., Eur J Echocardiogr 2009; 10(2):165-93; Evangelista A et al., Eur J Echocardiogr 2008; 9(4):438-48). Echocardiography was performed by expert physicians or sonographers at the sites. Echocardiography was done at screening, baseline, 6 hours after infusion start, 24 hours after infusion start (just before the end of infusion), and 48 hours after infusion start.

The following parameters were recorded for each patient at each timepoint and centrally measured by the CoreLab:

1. Cardiac dimension measures:
   a. Left ventricle end diastolic diameter (EDD): measured with M-mode echocardiography at the level of mitral valve (MV) leaflets from parasternal long axis view (PLAX) (normal range [NR]: 42-59 mm males and 39-53 mm females);
   b. Left ventricle end systolic diameter (ESD): measured with M-mode echocardiography at the level of mitral valve (MV) leaflets from PLAX (NR: 25-35 mm);
   c. Left ventricle end diastolic volume (EDV): measured with M-mode echocardiography at the level of mitral valve (MV) leaflets from PLAX (NR: 67-155 mL males and 56-104 mL females);
d. Left ventricle end systolic volume (ESV): measured with M-mode echocardiography at the level of mitral valve (MV) leaflets from PLAX (NR: 22-58 mL males and 19-49 mL females);
e. Left atrium diameter (LAD): measured at end-ventricular systole with M-mode echocardiography from PLAX. (NR: 30-40 mm males and 27-38 mm females)
f. Left atrium area (LAA): measured from apical four chamber view (NR: 520 cm$^2$); and
g. Left atrium volume (LAV): derived from area-length measured from apical four chamber view (NR: 18-58 mL males and 22-52 mL females).

2. Left ventricle diastolic function parameters:
a. E wave: measured from mitral valve pulsed wave Doppler, is the peak velocity of early filling. Normal range for all the diastolic parameters significantly changes with age;
b. A wave: measured from mitral valve pulsed wave Doppler is the peak velocity of late atrial filling. Not evaluable in patients with AF;
c. E wave deceleration time (EDT): measured from mitral valve pulsed wave Doppler represent the slope of the descending part of E wave;
d. E/A ratio: determines the type of diastolic filling pattern (normal E/A=1-2 and EDT=150-200 ms, abnormal relaxation E/A<1 and EDT2:240 ms, pseudonormal E/A=0.8-1.5; restrictive E/A22 and EDT<160 ms). Not evaluable in patients with AF;
e. Ea: measured with tissue Doppler method at the lateral and septal side of the mitral annulus from apical four chamber view is the early diastolic velocity. The value has been calculated as the average between Ea lateral and Ea septal. (NR210 cm/s) (see Nagueh S F et al., Eur J Echocardiogr. 2009; 10(2): 165-93);
f. Aa: measured with tissue Doppler method at the lateral and septal side of the mitral annulus from apical four chamber view is the late atrial diastolic velocity. The value has been calculated as the average between Aa lateral and Aa septal. Not evaluable in patients with AF; and
g. E/Ea ratio: this is a derived measure from E and Ea value. This is highly correlated with left ventricle filling pressure and with prognosis in patients with HF. (NR: <13) (see Nagueh S F et al., supra).

3. Left ventricle systolic function parameters:
a. Left ventricle ejection fraction (LVEF): measured with Simpson biplane method according to international recommendations from apical four chamber view and apical two chamber view. (NR 255%) (see Lang R M et al., J Am Soc Echocardiogr. 2005; 18(12):1440-63); and
b. Sa: measured with tissue Doppler method at the lateral and septal side of the mitral annulus from apical four chamber view. The value has been calculated as the average between Sa lateral and Sa septal. Validation studies demonstrated that Sa correlates with LVEF (NR 26 cm/s) (see Gulati V K et al., Am J Cardiol. 1996; 77(11):979-84).

4. Overall cardiac contraction parameters:
a. Stroke volume (SV): is a derived measure obtained with the application of Bernoulli's formula using the dimension of left ventricle outflow tract (LVOT) as diameter and LVOT time velocity integral as velocity. (NR>60 mL/beat);
b. Cardiac output (CO): is derived by the multiplication of SV×heart rate (HR) (NR: >4 L/min);
c. Stroke volume index (SVI): is a derived parameter obtained by the adjustment of SV by body surface area (BSA) (NR: 33-47 mL/beat/m$^2$); and
d. Cardiac index (CI): is a derived parameter obtained by the adjustment of CO by body surface area (BSA) (NR: 2.5-4 L/min/m$^2$).

5. Right ventricle function parameters:
a. Pulmonary arterial systolic pressure (PASP): estimated by the sum of the peak velocity at tricuspidal continuous wave Doppler and a fixed value derived from inferior vena cava diameter and respiratory change. (NR<35 mmHg);
b. Tricuspid annular plane systolic excursion (TAPSE): measured from M-mode echocardiography from apical four chamber view. TAPSE correlates with right ventricle ejection fraction and its reduction associated with worse prognosis in HF. (NR>16 mm) (see Ghio S et al., J Am Coll Cardiol 2001; 37(1):183-8); and
c. Right ventricle Sa: measured with tissue Doppler method at right ventricle free wall from apical four chamber view. Sa is a derived parameter of systolic function and correlated with right ventricle ejection fraction. (NR>10 cm/s) (see Voelkel N F et al., Circulation 2006; 114(17):1883-91; Haddad F et al., Circulation 2008; 117(13):1717-31).

6. Other parameters:
a. Mitral regurgitation (MR): evaluated with a visual qualitative assessment ang graded in four categories: none, mild, moderate, and severe (see Lancellotti P et al., Eur J Echocardiogr 2010; 11(4):307-32); and
b. Inferior vena cava diameter (IVC): measured with M-mode echocardiography from subcostal view at 1-2 cm from the junction with right atrium. This parameter has been used to estimate systolic pulmonary artery pressure. It correlated with right atrium pressure indicating the grade of congestion. Increased IVC diameter is associated with prognosis in patients with HF (NR: 51.5 cm) (see Pellicori P et al., JACC Cardiovasc Imaging 2013; 6(1):16-28; Voelkel N F et al., Circulation 2006; 114(17):1883-91).

TABLE 1A

Cardiac changes at 6 hours of infusion.

| Parameter | Ista 0.5 µg/kg/min | Ista 1.0 µg/kg/min | Placebo | p Ista 0.5 | p Ista 1.0 |
|---|---|---|---|---|---|
| LAA (cm$^2$) | −0.33 ± 1.885 | −0.84 ± 2.421 | −0.52 ± 1.840 | 0.663 | 0.521 |
| LAV (ml) | −1.16 ± 11.265 | −4.92 ± 14.390 | −3.24 ± 10.047 | 0.399 | 0.558 |

TABLE 1A-continued

Cardiac changes at 6 hours of infusion.

| Parameter | Ista 0.5 μg/kg/min | Ista 1.0 μg/kg/min | Placebo | p Ista 0.5 | p Ista 1.0 |
|---|---|---|---|---|---|
| Diastolic function | | | | | |
| E wave (cm/s) | −3.33 ± 14.764 | −9.13 ± 17.464 | −1.10 ± 10.990 | 0.451 | 0.018 |
| A wave (cm/s) | 1.76 ± 13.572 | 5.56 ± 17.280 | 1.55 ± 10.368 | 0.955 | 0.348 |
| EDT (ms) | 6.83 ± 47.921 | 20.37 ± 50.849 | −0.18 ± 38.939 | 0.491 | 0.052 |
| E/A ratio | −0.286 ± 0.866 | −0.317 ± 0.898 | −0.124 ± 0.866 | 0.566 | 0.458 |
| e' (cm/s) | 0.61 ± 1.010 | 0.01 ± 1.154 | 0.25 ± 1.167 | 0.146 | 0.376 |
| E/e' ratio | −3.183 ± 5.628 | −2.028 ± 3.652 | −0.740 ± 3.994 | 0.032 | 0.150 |
| Systolic function | | | | | |
| Sa (cm/s) Left V | 0.613 ± 1.035 | 0.908 ± 0.936 | 0.197 ± 0.919 | 0.065 | 0.001 |
| S (cm/s) Right V | 1.25 ± 2.185 | 2.00 ± 1.907 | 0.43 ± 1.441 | 0.125 | 0.003 |
| Cardiac function | | | | | |
| CO (l/min) | 0.385 ± 0.843 | 0.228 ± 0.760 | 0.083 ± 0.705 | 0.094 | 0.390 |
| CI (l/min/m2) | 0.209 ± 0.445 | 0.140 ± 0.434 | 0.042 ± 0.400 | 0.090 | 0.309 |
| SV (ml/beat) | 7.724 ± 11.752 | 7.269 ± 8.134 | 2.405 ± 7.244 | 0.020 | 0.007 |
| SVI(ml/beat/m2) | 4.198 ± 6.218 | 4.187 ± 4.641 | 1.317 ± 4.077 | 0.019 | 0.005 |

TABLE 1B

Cardiac changes at 24 hours of infusion.

| Parameter | Ista 0.5 μg/kg/min | Ista 1.0 μg/kg/min | Placebo | p Ista 0.5 | p Ista 1.0 |
|---|---|---|---|---|---|
| LAA (cm$^2$) | −1.70 ± 2.463 | −2.56 ± 2.972 | −0.31 ± 1.886 | 0.008 | <0.001 |
| LAV (ml) | −7.94 ± 13.269 | −13.81 ± 17.198 | −2.95 ± 10.624 | 0.079 | 0.002 |
| Diastolic function | | | | | |
| E wave (cm/s) | −8.14 ± 17.640 | −14.24 ± 24.416 | −4.16 ± 12.502 | 0.267 | 0.031 |
| A wave (cm/s) | 5.13 ± 10.990 | 11.10 ± 16.498 | −1.14 ± 7.580 | 0.045 | 0.003 |
| EDT (ms) | 12.88 ± 54.954 | 9.79 ± 52.212 | 4.58 ± 35.759 | 0.456 | 0.628 |
| E/A ratio | −0.647 ± 0.812 | −0.722 ± 1.068 | −0.164 ± 0.833 | 0.005 | 0.004 |
| e' (cm/s) | 0.94 ± 1.089 | 0.91 ± 1.792 | 0.26 ± 1.23 | 0.013 | 0.635 |
| E/e' ratio | −4.548 ± 4.754 | −3.191 ± 2.623 | −1.285 ± 3.351 | 0.001 | 0.011 |
| Systolic function | | | | | |
| Sa (cm/s) Left V | 0.679 ± 0.907 | 0.803 ± 1.023 | 0.171 ± 1.029 | 0.024 | 0.012 |
| S (cm/s) Right V | 1.10 ± 1.780 | 1.55 ± 2.012 | 0.15 ± 1.424 | 0.052 | 0.015 |
| Cardiac function | | | | | |
| CO (l/min) | 0.486 ± 0.696 | 0.239 ± 0.786 | 0.195 ± 0.651 | 0.073 | 0.797 |
| CI (l/min/m2) | 0.264 ± 0.369 | 0.140 ± 0.443 | 0.116 ± 0.373 | 0.097 | 0.808 |
| SV (ml/beat) | 9.725 ± 12.192 | 9.339 ± 8.875 | 4.039 ± 6.259 | 0.015 | 0.005 |
| SVI(ml/beat/m2) | 5.333 ± 6.664 | 5.318 ± 4.955 | 2.336 ± 3.516 | 0.019 | 0.005 |

TABLE 1C

Cardiac changes a 48 hours of infusion.

| Parameter | Ista 0.5 μg/kg/min | Ista 1.0 μg/kg/min | Placebo | p Ista 0.5 | p Ista 1.0 |
|---|---|---|---|---|---|
| Diastolic function | | | | | |
| E/A ratio | −0.278 ± 1.043 | −0.356 ± 0.967 | −0.172 ± 0.741 | 0.729 | 0.509 |
| E/e' ratio | −2.570 ± 3.654 | −2.218 ± 3.193 | −1.800 ± 4.013 | 0.388 | 0.629 |
| Systolic function | | | | | |
| LVEF (%) | 1.28 ± 3.693 | 2.06 ± 4.975 | 1.24 ± 3.539 | 0.968 | 0.427 |
| Sa (cm/s) | 0.224 ± 0.811 | 0.257 ± 0.771 | 0.132 ± 0.898 | 0.640 | 0.525 |
| Cardiac function | | | | | |
| CO (l/min) | 0.350 ± 0.788 | 0.368 ± 0.735 | −0.017 ± 0.691 | 0.041 | 0.026 |
| CI (l/min/m$^2$) | 0.191 ± 0.426 | 0.205 ± 0.407 | −0.007 ± 0.384 | 0.044 | 0.027 |
| SV (ml/beat) | 4.815 ± 9.832 | 5.203 ± 8.078 | 1.787 ± 7.108 | 0.139 | 0.062 |
| SVI (ml/beat/m$^2$) | 2.762 ± 5.603 | 2.913 ± 4.572 | 1.039 ± 4.026 | 0.139 | 0.071 |

The quantitative determination of PST 2744 and its metabolite PST 2915 in human plasma was determined by the HPLC-MS/MS method that included a mobile phase of 70:30 acetonitrile/water, 1 mL/L 1M formic acid, and 1 mL/L 5M ammonium acetate. The flow rate was 1 mL/min, and the chromatographic separation was by reversed phase HPLC (Column: SYNERGI 4μ POLAR-RP80A 150×4.6 mm equipped with a Security-guard Phenomenex Polar-RP 4×3 mm). Detection was performed by MS/MS, and the acquisition mode was Multiple Reaction Monitoring (MRM).

The quantitative determination of istaroxime metabolies PST 2922 and PST 3093 in human plasma was also measured by the HPLC-MS/MS method. In this case, the mobile phase was 50:50 $H_2O/CH_3CN$ (v/v) and 500 μL/L 98-100% HCOOH. The flow rate was 1 mL/min and chromatographic separation was done by reversed-phase HPLC (Column: Phenomenex Phenyl hexyl, 150×4.6 mm, equipped with a Phenomenex phenyl propyl guard-cartridge) under isocratic conditions. Detection was performed by MS/MS (376.0→282.0 amu for PST2922, 378.0→284.0 amu for PST 3093 and 362.0→268.0 amu for PST 3418, IS).

The data reported in Table 1A clearly indicates that infusion at either 0.5 μg/kg/min or 1 μg/kg/min istaroxime does not significantly improve most of the altered echo parameters of diastolic function (E, A waves, E/A ratio), with significant reduction occurring only with E/e' at 0.5 μg/kg/min. The systolic function (Sa and S wave) is improved at 1 μg/kg/min.

Surprisingly, when istaroxime was infused for 24 hours, a clear and statistically significant improvement is observed for most of the diastolic function parameters (E and A waves, E/A and E/e' ratios), while the positive effect of systolic function (Sa and S wave) is maintained but does not continue to increase (see Table 1B). At 48 hours, both the CO and CI changes are still significantly increased over placebo (see Table 1C). The shift from increased changes of SV and SVI at 6 and 24 hours to changes in CO and CI at 48 hours is also favoured by the normalization of the decreased HR at 6 and 24 hours, which was demonstrated in the previous Horizon study and confirmed in the present study. The changes of the other indexes of cardiac relaxation and contraction are still present, but do not achieve the statistical significance.

FIGS. 2A-2C show the plasma concentrations of istaroxime and its metabolites in Caucasian and Chinese patients during and subsequent to infusion with 0.5 or 1 μg/kg/min of istaroxime for 24 hours. During the infusion period, both istaroxime (2744) and istaroxime metabolite PST 2922 remain relatively constant and are rapidly cleared after infusion is stopped. On the other hand, istaroxime metabolites PST 2915 and PST 3093 continue to accumulate in the plasma throughout the infusion period with the average concentration of PST 3093 exceeding 60 ng/mL by the end of the infusion period and with average concentration levels exceeding 10 ng/mL even at 70 hours, or 46 hours post-infusion.

Notably, at 48 hours of infusion, the plasma levels of istaroxime are not detectable after 20 hours, while those of metabolite PST 3093 average about 25.02 ng/ml in Caucasian patients after 0.5 μg/kg/ml istaroxime infusion, about 12.5 ng/ml in Chinese patients after 0.5 μcg μg/kg/ml istaroxime infusion, and about 21.2 ng/ml with 1 μg/kg/ml istaroxime infusion (see FIGS. 2A-2C). These concentrations are much higher than the concentrations of 3093 exhibiting SERCA2a-stimulatory activity in SR vesicles from normal canine heart as shown in Table 3. Moreover, according to Ferrandi M et al. (BJP 2013; 169:1849-1861), istaroxime exerts its maximum SERCA2a activation in SR vesicles from failing canine hearts at concentrations that are much lower (about 10 times) than those able to stimulate this activity in SR vesicles from healthy canine heart. Therefore, it is likely that this remarkable difference between normal and failing heart SR vesicles may also occur for PST 3093, which may continue to maintain its SERCA2a stimulatory activity even at the lower concentrations detected at 72 hours (see FIGS. 2A-2C), where no echocardiographic data are available.

While not intending to be bound by theory, the above-discussed observation is consistent with the hypothesis that a pure SERCA2a activator may improve cardiac pump function. Finally this change in efficacy of cardiac pump function is not associated with any significant changes in plasma level of Hs TnT, which is considered by cardiologists as the most reliable biomarker of myocardial damage. This lack of Hs TnT change is likely due the activation of SERCA2a that, by reducing the cardiomyocytes plasma $Ca^{2+}$ concentration, also minimizes the cardiomyocytes damage. At present, the stimulation of the cardiac pumping ability by the only available inotropic agent under development (omecamtiv) is associated with an increase in the plasma levels of Hs TnT, and different developmental strategies are under study to detect the dose that minimize these changes in plasma HsTnT (Teerlink J R et al., 2016 Lancet 388, 2895-903).

The present invention may provide the basis for planning appropriate trials aimed at assessing whether different ratios between plasma levels of PST 3093 and istaroxime, achievable by varying the dose and duration of istaroxime infusion, may furnish greater therapeutic benefits to patients with HFpEF or HFmEF than to patients with HFrEF, or in patients with or without Echocardiographic indexes revealing a status of diastolic impairment; thus increasing the precision of the therapeutic approach to AHF.

Pharmaceutical Compositions

Pharmaceutical compositions and formulations for intravenous infusion comprising istaroxime or a metabolite thereof in admixture with at least one conventional pharmaceutically acceptable carrier and/or vehicle and/or excipient are commonly known in the art.

The pharmaceutical compositions and formulations for intravenous infusion can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Mack Publishing Co, Easton PA ("Remington's").

The formulations may conveniently be presented in unit dosage form and may be prepared by any method known in the art of pharmacy. The amount of active ingredient which can be combined with a carrier or vehicle material to produce a single dosage form will vary depending upon the subject being treated and the particular mode of administration. The amount of active ingredient that can be combined with a carrier material to produce a single dosage form will generally be the amount of the compound which produces a therapeutic effect.

Pharmaceutical formulations as provided herein can be prepared according to any method known to the art for the manufacture of pharmaceuticals. Such formulations can contain additional agents, such as preserving or stabilizing agents. A formulation can be admixtured with nontoxic pharmaceutically acceptable carriers or excipients which are suitable for manufacture. Formulations may comprise one or more diluents, emulsifiers, preservatives, buffers, excipients, etc. and may be provided in such forms as liquids, powders, emulsions, lyophilized powders, etc.

Aqueous suspensions can contain an active agent (e.g., a composition used to practice the uses and methods as provided herein) in admixture with excipients suitable for the manufacture of aqueous suspensions. Such excipients include a suspending agent, such as sodium carboxymethylcellulose, methylcellulose, hydroxypropyl-methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate. Formulations can be adjusted for osmolarity.

According to the present invention, istaroxime is given by intravenous (IV) administration. These formulations can comprise a solution of active agent dissolved in a pharmaceutically acceptable carrier. Acceptable vehicles and solvents that can be employed are water, dextrose in water, and Ringer's solution, an isotonic sodium chloride. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. The administration is by bolus or continuous infusion (e.g., substantially uninterrupted introduction into a blood vessel for a specified period of time).

Istaroxime as provided herein can be lyophilized. Provided herein is a stable lyophilized formulation comprising a composition as provided herein, which can be made by lyophilizing a solution comprising a pharmaceutical as provided herein and a bulking agent, e.g., mannitol, trehalose, raffinose, and sucrose or mixtures thereof. There are many other conventional lyophilizing agents. Among the sugars, lactose is the most common. Also used are citric acid, sodium carbonate, EDTA, Benzyl alcohol, glycine, sodium chloride, etc. (see, for example, Journal of Excipients and Food Chemistry Vol. 1, Issue 1 (2010) pp 41-54; U.S. patent app. no. 20040028670). In a preferred embodiment, istaroxime can be prepared as powder for injection according to the teaching of CN103315968.

According to the present invention, istaroxime as provided herein can be administered for prophylactic and/or therapeutic treatments. In therapeutic applications, compositions are administered to a subject already suffering from a condition, or disease in an amount sufficient to treat, prevent, cure, alleviate or partially arrest the clinical manifestations of the condition, or disease and its complications (i.e., a "therapeutically effective amount"). For example, in alternative embodiments, pharmaceutical compositions as provided herein are administered in an amount sufficient to treat, prevent or ameliorate in an individual in need thereof. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' bioavailability, metabolism, clearance, and the like (see, e.g., Hidalgo-Aragones J., Steroid Biochem. Mol. Biol. 1996; 58:611-617; Groning, Pharmazie 1996; 51:337-341; Fotherby Contraception 1996; 54:59-69; Johnson, J. Pharm. Sci. 1995; 84:1144-1146; Rohatagi, Pharmazie 1995; 50:610-613; Brophy, Eur. J. Clin. Pharmacol. 1983; 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regimen, i.e., dose schedule and dosage levels, administered practicing the methods as provided herein are correct and appropriate.

Single or multiple administrations of formulations can be given depending on the dosage and frequency as required by the AHF clinical symptoms of patient. The formulations should provide a sufficient quantity of active agent to effectively treat or prevent or ameliorate a conditions, diseases or symptoms as described herein. A correct treatment of AHF, by selectively normalizing a depressed biochemical activity underlying the symptoms of subset of patients (HFpEF or HFmEF), may be expected to selectively improve the symptoms and to reduce the incidence of unwanted side effects produced by the available drugs either during hospital staying or after discharge. The term prevention is applicable when the continuous monitoring of the pulmonary pressure is possible with the appropriate chronic implantable devices that furnish and estimation of PCWP. In this condition a significant increase in the PCWP may precede the appearance of symptoms of AHF, thus providing the rational to infuse the Istaroxime at the right dose to prevent the symptoms and the consequent hospitalization In one embodiment, an effective amount of istaroxime or an equivalent of a pharmaceutically acceptable salt, solvate or hydrate thereof, administered to an individual in need thereof comprises use of various dosing schedules, e.g.: from about 0.1 µg/kg/min to about 3.0 µg/kg/min, e.g., 0.1 µg/kg/min, 0.15 µg/kg/min, 0.2 µg/kg/min, 0.25 µg/kg/min, 0.3 µg/kg/min, 0.35 µg/kg/min, 0.4 µg/kg/min, 0.5 µg/kg/min, 0.6 µg/kg/min, 0.7 µg/kg/min, 0.8 µg/kg/min, 0.9 µg/kg/min, 1.0 µg/kg/min, 1.1 µg/kg/min, 1.2 µg/kg/min, 1.3 µg/kg/min, 1.4 µg/kg/min, 1.5 µg/kg/min, 1.6 µg/kg/min, 1.7 µg/kg/min, 1.8 µg/kg/min, 1.9 µg/kg/min, 2.0 µg/kg/min, 2.1 µg/kg/min, 2.2 µg/kg/min, 2.3 µg/kg/min, 2.4 µg/kg/min, 2.5 µg/kg/min, 2.6 µg/kg/min, 2.7 µg/kg/min, 2.8 µg/kg/min, 2.9 µg/kg/min, or 3.0 µg/kg/min. For instance, in some embodiments, istaroxime or its metabolite (e.g., PST 3093), is administered by infusion at an effective dose from about 0.2 µg/kg/min to about 2.0 µg/kg/min, or from about 0.2 µg/kg/ min to about 1.5 µg/kg/min, or from about 0.25 µg/kg/min to about 1.0 µg/kg/min, or from about 0.5 µg/kg/min to about 1.0 µg/kg/min.

In alternative embodiments, an effective amount of istaroxime or an equivalent of a pharmaceutically acceptable salt, solvate or hydrate thereof, administered to an individual in need thereof is individualized based on basal levels and subsequent changes of certain heart function parameters, such as echo indexes or Pulmonary Capillary Wedge Pressure (PCWP), dyspnea, peripheral and pulmonary venous congestion, urinary volume, serum biomarkers such as NT-proBNP and high sensitive cardiac Troponin (hs-cTnT).

In alternative embodiments, an effective amount is demonstrated by reduction of PCWP, orthopnea, paroxysmal nocturnal dyspnea, reduction of peripheral and pulmonary venous congestion, such as pulmonary crepitations or rales, reduction of ankle swelling, reduction of biomarkers urinary output such as NT-proBNP and high sensitive cardiac Troponin (hs-cTnT).

In alternative embodiments, an effective amount of istaroxime or an equivalent of a pharmaceutically acceptable salt, solvate or hydrate thereof, administered to an individual in need thereof is individualized based on basal levels and subsequent changes of certain heart function parameters, such as echo indexes or Pulmonary Capillary Wedge Pressure (PCWP), dyspnea, peripheral and pulmonary venous congestion, urinary volume, serum biomarkers such as NT-proBNP and high sensitive cardiac Troponin (hs-cTnT).

In alternative embodiments, an effective amount is demonstrated by reduction of PCWP, orthopnea, paroxysmal nocturnal dyspnea, reduction of peripheral and pulmonary venous congestion, such as pulmonary crepitations or rales, reduction of ankle swelling, reduction of biomarkers urinary output such as NT-proBNP and high sensitive cardiac Troponin (hs-cTnT).

Methods of Treatment

Also provided herein are methods of treating an individual with heart failure. In preferred embodiments, the individual exhibits symptoms of, or has been diagnosed with, acute heart failure. While the individual can be a non-human animal, in a preferred embodiment, the individual is a human patient, such as a human patient suffering from heart failure.

In general, the compositions described herein can be used to treat the individual having heart failure or acute heart failure. In an embodiment, the method of therapy includes providing or presenting the individual having heart failure or acute heart failure. In some cases, a measuring step is first carried out to determine the baseline heart function of the individual. For instance, an individual with heart failure may exhibit impaired or decreased diastolic relaxation function. The measuring step may include measuring one or more parameters of heart failure, such as, but not limited to, decreased heart rate, decreased heart pressure, decreased systolic and/or diastolic blood pressure, reduced left ventricular end-diastolic/systolic volume and function (LVEF), or increased E/Ea or E/A ratios reduced Ea ratio decreased stroke volume. As one having ordinary skill in the art will appreciate, any suitable measuring technique available in the art at the time of the measuring step is suitable for use herein, and it is well within the purview of such skilled artisan to select an appropriate measuring technique corresponding to the parameter of interest. A non-limiting list of suitable measuring equipment/techniques includes echocardiogram, cardiac catheterization, nuclear stress test, CAT scan, radionuclide ventriculography scan, stethoscope, sphygmomanometer, and the like. For instance, the diastolic relaxation can be measured by echocardiography or PCWP.

The methods disclosed herein also include administering to the individual a therapeutically effective amount of istaroxime or a metabolite thereof, such as PST 3093. In preferred embodiments, the istaroxime or istaroxime metabolite is in a pharmaceutical composition, such as any one of the combinations discussed above. The istaroxime or istaroxime metabolite is administered in an therapeutically effective dose as disclosed elsewhere herein, e.g., between about 0.25 µg/kg/min to about 1.0 µg/kg/min. In a more preferred embodiment, the route of administration is infusion, such as intravenous fusion. The measuring step can be performed before, during, or after the administering step. For instance, it may be desired to continually monitor one or more of the parameters of heart function during treatment and for a period of time thereafter.

As discussed above, it has been surprisingly discovered that administering istaroxime (or its metabolites) by infusion for an infusion duration of greater than 6 hours, e.g., 6.1 h, 6.2 h, 6.3 h, 6.4 h, 6.5 h, 6.6 h, 6.7 h, 6.8 h, 6.9 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 26 h, 27 h, 28 h, 29 h, 30 h, 31 h, 32 h, 33 h, 34 h, 35 h, 36 h, 37 h, 38 h, 39 h, 40 h, 41 h, 42 h, 43 h, 44 h, 45 h, 46 h, 47 h, or 48 h or more, results in increased SERCA2a activity and improving diastolic relaxation without causing arrhythmogenic effects due to, for example, $Na^+/K^+$ pump inhibition. In this manner, istaroxime infusion for greater than 6 hours exerts a lusitropic-SERCA2a activity that is prevailing on the inotropic activity and results in improved diastolic relaxation as compared to istaroxime infusion for less than 6 hours.

While not intending to be bound by theory, it is believed that this later-arising "pure" SERCA2a activation is due to an accumulation of istaroxime metabolites in the plasma of the individual. As such, in some embodiments, istaroxime is administered via intravenous infusion for a period of time sufficient to enable the accumulation of istaroxime metabolites in the plasma of the individual. In preferred embodiments, the infusion duration is sufficient to allow for the accumulation of one or more istaroxime metabolites; preferably, the metabolite is PST 2915 having the structural formula (II) or PST 3093 having the structural formula (III); more preferably, the metabolite is PST 3093. In some embodiments, the accumulation of istaroxime metabolite in the plasma is at a concentration of least about 3 ng/mL, e.g., 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 35 ng/mL, 40 ng/mL, 45 ng/mL, 50 ng/mL or more for a period of time of at least about 3 hours, e.g., 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h or more. In one embodiment, the istaroxime metabolite accumulates in the plasma to the desired concentration within 6 hours; preferably, within 3 hours or within 2 hours or within 1 hour of istaroxime infusion initiation and is maintained at or above that concentration for at least about 3 additional hours, e.g., 3, 4, 5, 6, 7, 8, 9, 10, 11, 12, 13, 14, 15, 16, 17, 18, 19, 20, 21, 22, 23, 24, or more additional hours; preferably, for at least 6 additional hours; more preferably for at least about 12 additional hours. In some embodiments, the desired plasma concentration of metabolite is at least about 5 ng/mL. In another embodiment, the istaroxime metabolite accumulates in the plasma to a concentration of at least about 10 ng/mL and is maintained at or above that concentration for at least about 6 additional hours; preferably for at least about 12 additional hours. In yet another embodiment, the istaroxime metabolite accumulates in the plasma to a concentration of at least about 15 ng/mL and is maintained at or above that concentration for at least about 6 additional hours; preferably for at least about 12 additional hours. In some embodiments, the plasma concentration of the metabolite remains above 5 ng/mL for at least about 6 hours following the completion of the istaroxime administration. In some embodiments, the plasma concentration of the metabolite remains above 10 ng/mL for at least about 6 hours following the completion of the istaroxime administration. In yet other embodiments, the plasma concentration of the metabolite remains above 20 ng/mL for at least about 6 hours following the completion of the istaroxime administration. In others, the concentration remains at least about 30 ng/mL, 40 ng/mL, or 50 ng/mL for an additional 6 hours or more, e.g., 6 h, 7 h, 8 h, 9 h, 10 h, 11 h, 12 h, 13 h, 14 h, 15 h, 16 h, 17 h, 18 h, 19, 20 h, 21 h, 22 h, 23 h, 24 h or more following istaroxime infusion. For instance, the metabolite accumulation may remain at a concentration level of at least about 10 ng/mL for an additional 12 hours or more, e.g., 12 h, 13 h, 14 h, 15 h, 16 h, 17 h, 18 h, 19, 20 h, 21 h, 22 h, 23 h, 24 h, 25 h, 26 h, 27 h, 28 h, 29 h, 30 h, 31 h, 32 h, 33 h, 34 h, 35 h, 36 h, 37 h, 38 h, 39 h, 40 h, or more following the istaroxime infusion.

As one having ordinary skill in the art would appreciate, the plasma concentration of istaroxime or istaroxime metabolite can be measured by conventional means, such as by HPLC-MS/MS.

In some embodiments, the istaroxime metabolites have the structural formulas (II) or (III):

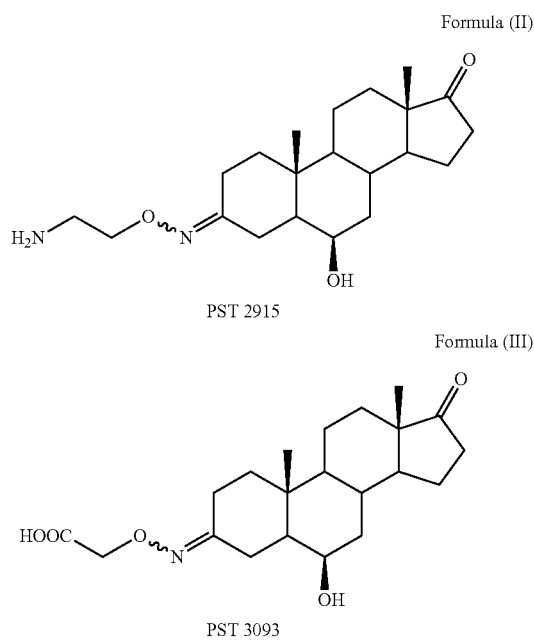

Formula (II)

PST 2915

Formula (III)

PST 3093

In preferred embodiments, the metabolite of istaroxime is the compound PST 3093.

In a further example, an individual is diagnosed with heart failure or acute heart failure, and is administered about 0.25 µg/kg/min to about 1.0 µg/kg/min of istaroxime for a period of time that is greater than 6 hours. As the istaroxime is metabolized by the individual, istaroxime metabolites, such as PST 3093, begin to accumulate in the plasma of the individual. For instance, istaroxime metabolite PST 3093 may accumulate to a plasma concentration of at least about 5 ng/mL within 3 hours of istaroxime infusion and is maintained at a plasma level of at least about 5 ng/mL for the duration of the istaroxime infusion and for an additional 6 to about 36 hours. The presence of the PST 3093 acting as a "pure" SERCA2a activator confers to the individual improved diastolic relaxation.

In some embodiments, the method of treatment may include administration of the istaroxime metabolite by infusion in combination with or instead of istaroxime. For instance, a method of treating an individual with heart failure is disclosed that includes administering to the individual a therapeutically effective amount of a pharmaceutical composition that comprises a pharmaceutically acceptable carrier and an istaroxime metabolite having the formula (II) or (III). In preferred embodiments, PST 3093 or PST 2915 is the metabolite; more preferably, it is PST 3093. Such methods may include a measuring step, wherein one or more parameters of heart function are measured using measuring techniques available in the art. The measuring step may be performed prior to, during, or subsequent to the administration of the pharmaceutical composition. In such methods, the therapeutically effective dose of PST 3093 will be between about 0.2 µg/kg/min to about 2.0 µg/kg/min; preferably between about 0.3 µg/kg/min and about 1.5 µg/kg/min; more preferably between about 0.5 µg/kg/min and about 1.0 µg/kg/min. In such methods, the duration of infusion will be greater than 6 hours, e.g., 6.1 h, 6.2 h, 6.3 h, 6.4 h, 6.5 h, 6.6 h, 6.7 h, 6.8 h, 6.9 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, or more.

In some embodiments, it is desired to treat an individual with acute heart failure with two or more istaroxime dose regimens to initially treat the acute heart failure symptoms and subsequently normalize the heart functional defects associated with a more chronic heart failure condition. In such embodiments, the dosing regimen is manipulated to control the istaroxime to metabolite ratio by starting with the administration by infusion of a higher dose of istaroxime to treat acute heart failure symptoms followed by administering a lower istaroxime dose by infusion for a longer duration to allow for the accumulation of istaroxime metabolites. In this manner, the initial infusion will allow for rapid SERCA2a stimulation and Na,K-ATPase inhibition resulting in a rapid positive inotropy to treat the acute heart failure symptoms, while the second infusion will allow for accumulation of the selective SERCA2a-activating istaroxime metabolite PST 3093 and extended positive inotropy at a reduced risk of arrhythmogenic $Ca^{2+}$ triggering events.

Therefore, provided herein is a method of treating an individual having acute heart failure, wherein it is administered to the individual by infusion a first pharmaceutical composition that includes a pharmaceutically acceptable carrier and istaroxime at a therapeutic dose of at least about 1.5 µg/kg/min. The heart function of the individual can be measured and monitored before, during, and/or after beginning infusion of the first pharmaceutical composition using any of the techniques discussed herein. For instance, in some embodiments, one or more parameters of heart function are measured prior to administering istaroxime in order to determine, e.g., whether the individual is presenting with HFpEF or HFmEF. In other embodiments, initial measurements may include echocardiogram or PCWP values to measure diastolic relaxation dysfunction. These measurements may also be initiated concurrently with administering the istaroxime by infusion and/or may be continued throughout the duration of the infusion. In some embodiments, the step of measuring one or more parameters of heart function can be performed after administering the first pharmaceutical composition.

In the dosing manipulation methods, once an improvement in the parameters of heart function are measured, a pharmaceutical composition that comprises a pharmaceutically acceptable carrier and istaroxime at a lower therapeutic dose is administered by infusion. For instance, an improvement in diastolic relaxation in the individual as measured by echocardiogram or PCWP as compared to the same measurements taken prior to and/or at the start of the initial infusion would indicate treatment of the acute heart failure symptoms. Also, the reduction of acute heart failure symptoms such as breathlessness, ankle swelling, elevated jugular venous pressure, pulmonary crackles and peripheral edema may justify the change in the infusion rate. In some embodiments, the second therapeutic dose of istaroxime is less than about 1.5 µg/kg/min; preferably between about 0.3 µg/kg/min and about 1.5 µg/kg/min; more preferably between about 0.5 µg/kg/min and about 1.0 µg/kg/min. For instance, in one particular embodiment, the second therapeutic dose of istaroxime is about 0.5 µg/kg/min. Administering by infusion of the second therapeutic dose of istaroxime may then be continued for a duration of greater than 6 hours, e.g., 6.1 h, 6.2 h, 6.3 h, 6.4 h, 6.5 h, 6.6 h, 6.7 h, 6.8 h, 6.9 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 36 h, 48 h, or more.

In some embodiments, the second, lower dose of istaroxime may be infused for a duration sufficient to produce an accumulated plasma concentration of an istaroxime metabolite, such as PST 3093. In such embodiments, infusion of the lower dose of istaroxime is continued until the plasma concentration of PST 3093 is at least about 20 ng/mL. In other embodiments, infusion of the lower dose of istaroxime is continued until the plasma concentration of PST 3093 is at least about 30 ng/mL. In still other embodiments, infusion is continued until the plasma concentration of PST 3093 is at least about 40 ng/mL or at least about 50 ng/mL or at least about 60 ng/mL. Once infusion of the lower dose of istaroxime is stopped, the istaroxime compound is cleared from the individual while the istaroxime metabolite exhibiting selective or "pure" SERCA2a activation (i.e., 3093) remains in the individual's bloodstream for extended periods of time to confer to the individual improved heart function with a much lower risk of arrhythmogenic triggering events.

In alternative embodiments, in evaluating the efficacy of a treatment, a treatment regimen or a particular dosage, or to determine if a treatment versus a maintenance dosage should be given, individuals, e.g., patients affected by acute or chronic heart failure, are subject to regular periodic screening for the presence and extent of organ and tissue involvement or damage, e.g., heart (ventricle dilatation, third heart sound cardiac hypertrophy), fatigue, tiredness, reduced exercise tolerance, increased time to recover after exercise, kidney (renal insufficiency, oliguria), lung (orthopnea, paroxysmal nocturnal dyspnea, tachypnea), ankle swelling, elevated jugular venous pressure. A thorough physical examination should be done at a time interval chosen by those experts in the treatment of a cardiovascular disease, in particular acute or chronic heart failure which would concentrate on cardiac, pulmonary and peripheral circulation functions. Accordingly, in alternative embodiments, therapy with istaroxime or an equivalent of a pharmaceutically acceptable salt, solvate or hydrate thereof as disclosed herein, is instituted as early as possible, preferably in emergency, to prevent the rapid evolution of symptoms and continued after patient's discharge for years, preferably during the whole life of the patient or at least a period consistent with the way other drugs are used in heart failure. As the result of monitoring of patient's conditions by the medical doctor, istaroxime long infusion, longer than 6 hours may be given the patient up to once/twice a month in order to prevent occurrence of acute episodes of heart failure, thus avoiding emergency rescue of the patient and lessening the probability of life-threatening episodes.

According to the present invention, uses and methods as provided herein can further comprise co-administration with other drugs or pharmaceuticals. In fact, the present invention selectively corrects a depressed cardiac biochemical function (namely the SERCA2a activity). This certainly contributes to relieving the existing HF clinical symptoms, with less unwanted side effects than those of the available therapies (just because the selectivity mentioned above). However, as CHF and AHF are complex clinical syndromes the present invention is potentially associable to existing and future drug classes and/or specific drugs such as: a) drug classes such as, ACE inhibitors, AIRBs, diuretics, Ca channel blockers, β blockers, *digitalis*, NO donors, vasodilators, SERCA2a stimulators, neprilysin (NEP) inhibitors, myosin filament activators, recombinant relaxin-2 mediators, recombinant NP protein, activators of the soluble Guanylate Cyclase (sGC), beta-arrestin ligand of Angiotensin II receptor; b) specific drugs: hydrochlorothyzide, furosemide, verapamil, diltiazem, carvedilol, metoprolol, hydralazine, eplerenone, spironolactone, lisinopril, ramipril, nitroglycerin, nitrates, digoxin, valsartan, olmesartan, telmisartan, candesartan, losartan, entresto, omecamtiv, sacubitril, serelaxin, ularitide, levosimendan, cinaciguat. Subjects suffering from heart failure treated with the above drugs and undergoing regular clinical monitoring, for example having their pulmonary blood pressure continuously monitored with implanted probes, can be guarded in order to predict episode of AHF that may be prevented by the infusion of Istaroxime according to the present invention.

Istaroxime as disclosed in the present invention, as used a therapeutic agent for treating acute heart failure, can be combined with other therapeutic agents used in the treatment of the same disease. Exemplary other therapeutic agents are diuretics, for example furosemide, bumetanide, and torasemide. Metolazone, an aldosterone antagonist, such as spironolactone or eplerenone; thiazide diuretics, such as Hydrochlorothiazide, metolazone, and chlorthalidone. Other agents are ACE inhibitors, for example Lisinopril and Ramipril. Also Angiotensin II receptor blockers (ARBs), such as valsartan, candesartan and losartan can be taken into consideration. Angiotensin receptor/neprilysin inhibitor (ARNI), sacubitril for example, are comprised. Other agents can be selected from Beta-blockers, such as carvedilol and metoprolol for example, or Vasodilators, for example Hydralazine, optionally combined with isosorbide dinitrate, Nitrates, as nitroglycerin, amlodipine and felodipine; non-dihydropyridines such as diltiazem or verapamil. The compounds of the present invention can also be combined with Digoxin, if needed. Other drugs, as Ivabradine and other Anticoagulant may be considered.

The compounds of the present invention can be combined with other therapeutic agents, in particular agents useful for treating cardiovascular diseases, more in particular in the combination therapy of heart failure. The combined active ingredients can be administered according to different protocols, decided by the medical doctor. According to an embodiment of the present invention, combination therapy can be carried out by administering istaroxime both at the same time or at different time of the further therapeutically active ingredient or ingredients. In case of concomitant administration, the compound of the present invention and the further active ingredient or ingredients can be each formulated in a respective pharmaceutical composition or in the same unitary dosage form. In the former case, the present invention provides a kit, in particular for the treatment of heart failure, comprising separate pharmaceutical compositions containing the compound of the present invention and the further active ingredient or ingredients, respectively. In another embodiment, the present invention provides a pharmaceutical unit dosage form kit, in particular for the treatment of acute heart failure, comprising compound of the present invention and the further active ingredient or ingredients in the same unit dosage form. Combination therapy according to the present invention provides advantageous treatment of heart failure due to the inotropic-lusitropic effect of istaroxime herein disclosed in addition to or synergically combined with the well-known therapeutic effect of the additional active agents herein disclosed.

Also provided are nanoparticles, nanolipoparticles, vesicles and liposomal membranes comprising compounds used to practice the uses and methods as provided herein, e.g., to deliver pharmaceutically active compounds and compositions as provided herein: istaroxime or a compound of formula (II) or formula (III) or an equivalent of a pharmaceutically acceptable salt, solvate or hydrate thereof, optionally combined with a further therapeutically active agent as disclosed above to a subject in need thereof. In alternative embodiments, these compositions are designed to target specific molecules, including biologic molecules, such as polypeptides, including cell surface polypeptides, e.g., for targeting a desired cell type, e.g., a myocyte or heart cell, an endothelial cell, and the like. A slow release of Istaroxime may provide a sufficient compound to selectively increase the plasma levels of the metabolite leaving the plasma levels of Istaroxime within very low ranges.

Provided are multilayered liposomes comprising compounds used to practice methods as provided herein, e.g., as described in Park, et al., U.S. application No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice uses and methods as provided herein.

Liposomes can be made using any method, e.g., as described in U.S. Pat. No. 4,534,899; or Park, et al., U.S. application No. 20070042031, including method of producing a liposome by encapsulating an active agent according to the present invention (or a combination of active agents), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice uses and methods as provided herein comprise a substituted ammonium and/or polyanions, e.g., for targeting delivery of istaroxime or an equivalent of a pharmaceutically acceptable salt, solvate or hydrate thereof used to practice methods as provided herein to a desired cell type, as described, e.g., in U.S. application No. 20070110798.

Provided are nanoparticles comprising compounds according to the present invention used to practice uses and methods as provided herein in the form of active agent-containing nanoparticles (e.g., a secondary nanoparticle), as described, e.g., in U.S. application No. 20070077286. In one embodiment, provided are nanoparticles comprising a fat-soluble active agent used to practice a use and method as provided herein or a fat-solubilized water-soluble active agent to act with a bivalent or trivalent metal salt.

In one embodiment, solid lipid suspensions can be used to formulate and to deliver compositions used to practice uses and methods as provided herein to mammalian cells in vivo, in vitro or ex vivo, as described, e.g., in U.S. application No. 20050136121.

The compositions and formulations used to practice the uses and methods as provided herein can be delivered by the use of liposomes or nanoliposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed, J. Microencapsul. 1996; 13:293-306; Chonn Curr. Opin. Biotechnol. 1995; 6:698-708; Ostro, Am. J. Hosp. Pharm. 1989; 46:1576-1587. A liposome formulation of istaroxime as disclosed in Eur J Pharm Biopharm. 2011; 79(2):285-93 is also provided in the present invention.

Delivery Vehicles

In alternative embodiments, any delivery vehicle can be used to practice the uses and methods as provided herein, e.g., to deliver the compounds provided herein to a subject in need thereof. For example, delivery vehicles comprising polycations, cationic polymers and/or cationic peptides, such as polyethyleneimine derivatives, can be used e.g. as described, e.g., in U.S. application No. 20060083737.

In one embodiment, a dried polypeptide-surfactant complex is used to formulate a composition used to practice a use and method as provided herein, e.g., as described in U.S. application No. 20040151766.

In one embodiment, a composition used to practice uses and methods as provided herein can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to polyphosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

The following examples further illustrate the present invention.

Example 1. Preparation of the Compounds of Formula (II) and (III)

Synthesis of PST 2915

Step 1: Hydroboration

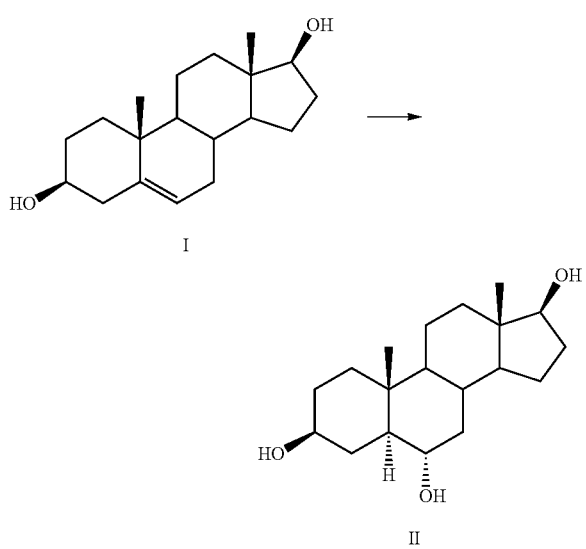

To a solution of dehydroepiandrosterone I (30.0 g) in 450 mL of THF maintained under a nitrogen atmosphere and at a temperature of −10° C. was added the complex BH·THF 1M in THF (260 mL). On completing the addition, the temperature was allowed to rise once again to ambient temperature; after 3 h 500 mL of $H_2O$ were added and then $NaBO_3 \cdot 4H_2O$ (31.4 g). The reaction was left to stir for one night. The precipitate formed was filtered, washed with THF and eliminated. The aqueous and organic phases were Separated, NaCl was added to the aqueous phase and this was re-extracted with THF (3×200 mL). The combined organic phases were anhydrified with NaCl and $Na_2SO_4$ and evaporated under reduced pressure to obtain the crude product, which was crystallised by AcOEt/MeOH and then filtered and washed with AcOEt. Approximately 21 g of androstane 3β, 6α, 17β-triol II were obtained (known product: Nicholson, S. H., Turner, A. B. J. Chem. Soc., Perkin Trans. 1, 1976, 1357 and U.S. Pat. No. 6,384,250 B2).

The analytical results are in agreement with those reported in the literature.

Step 2: Selective Oxidation.

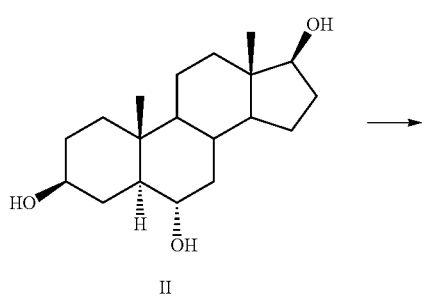

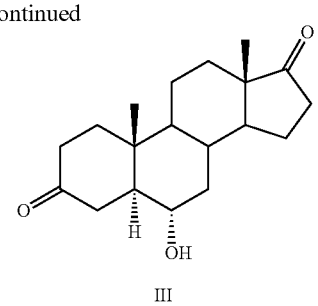

To a solution of Androstane 3β, 6α, 17β-triol II (30 grams) in a mixture composed by Dioxane (825 mL), Water (150 mL) and Pyridine (16.5 mL), N-Bromosuccinimide (52 grams) was added portion wise within 10 minutes protecting the vessel from light. The mixture was stirred for 16 hours at room temperature, diluted with 900 ml of water then $Na_2S_2O_3$ (15.5 grams) were added portion wise within 15 minutes. The solution was concentrated (around 1500 mL were removed) and the suspension was filtered and the solid dried under vacuum giving 28.1 grams of 6α-hydroxyandrostane-3,17-dione III (95% yield).

Step 3: Ketone Protection.

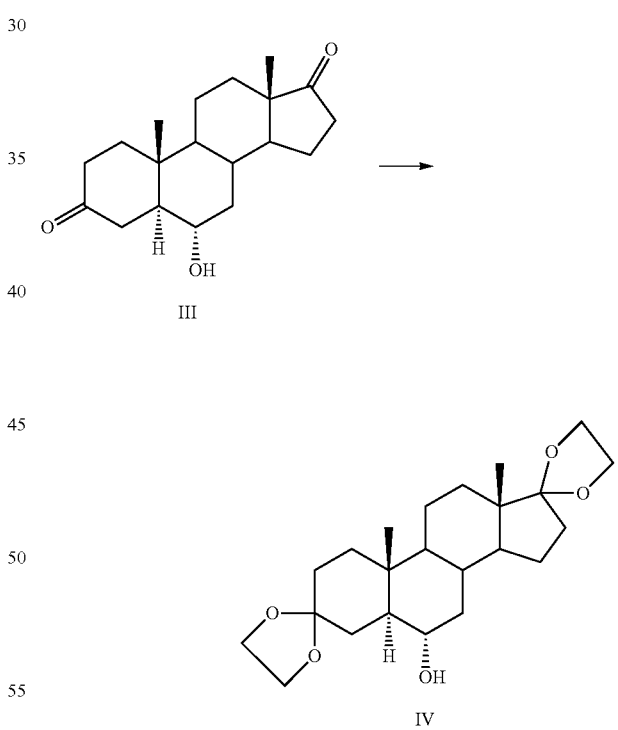

A suspension of 6α-hydroxyandrostane-3,17-dione III (18.85 grams) in 360 mL of glycol and P-Toluenesulfonic Acid (554 mg) was heated at 100° C. and distilled under vacuum to remove the azeotropic mixture glycol/water (around 5 mL). The mixture was cooled and treated with 250 mg of KOH dissolved in 25 ml of Methanol. 15 mL of water were added and, after stirring for 2 hours, the suspension was filtered giving intermediate IV as white solid (20.2 grams, 83% yield). The product was used without further purification.

Step 4: Oxidation.

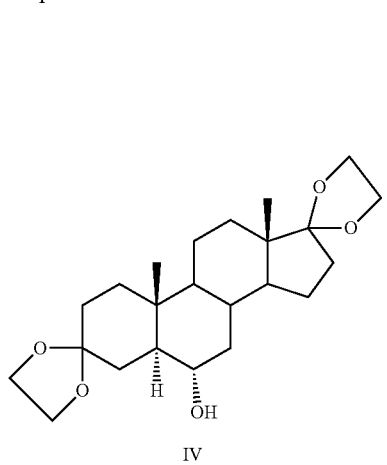

IV

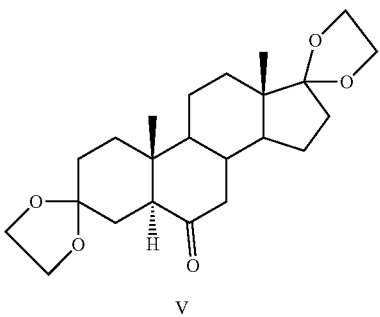

V

A solution constituted by 3 mL of Sodium Hypochlorite (6%) and 28 mL of Ethyl Acetate were stirred at room temperature and 27 mg of RuO$_2$ hydrate were added. When all the catalyst Ruthenium was solubilized the product IV (1 gram) was added portion wise waiting for the disappearance of black suspension. After 1 hour additional 3 ml of Sodium Hypochlorite (6%) were added and the clear solution stirred for 3 hours at room temperature. When the reaction is completed the mixture was filtered on a Celite pad and the aqueous phase was extracted with AcOEt. The combined organic phases were washed with a solution of NaHCO$_3$ (5% in water) and with NaCl (10% in water). The organic layer was dried over Na$_2$SO$_4$ and evaporated to dryness giving intermediate V (950 mg, 94% yield).

Step 5: Reduction.

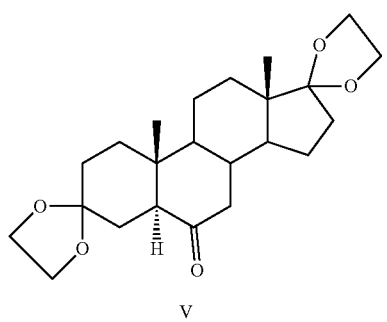

V

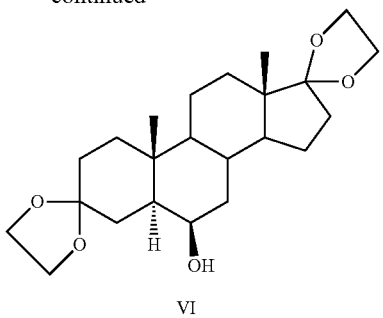

VI

A suspension of product V (5.76 grams) in Methanol (72 mL) was stirred at 0° C. and NaBH$_4$ (730 mg) was added. After 2 hours the reaction was completed, and the solvent was removed under reduced pressure. The crude product was suspended in 30 mL of water and extracted with CH$_2$Cl$_2$. The organic layer was dried over Na$_2$SO$_4$ and evaporated to dryness. The crude solid was purified by flash chromatography (SiO$_2$, Cyclohexane/AcOEt 7/3 as eluent) giving the product VI (5.16 grams, 89% yield).

Step 6: Ketone Deprotection.

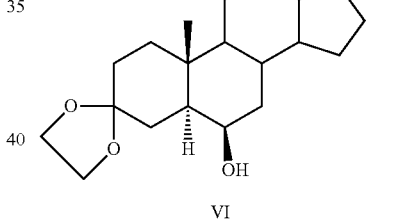

VI

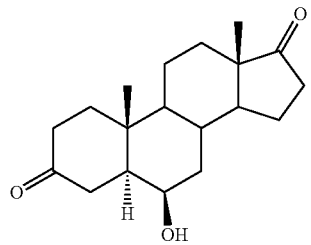

VII

To a stirred solution of product VI (2.85 grams) in 350 mL of distilled Acetone, P-toluenesulfonic acid (7.14 grams) was added. After 3 hours at room temperature a 5% solution of NaHCO$_3$ was added and the solvent was removed under reduced pressure. The product was extracted with CH$_2$Cl$_2$. The organic layer was dried over Na$_2$SO$_4$ and evaporated to dryness, giving the intermediate VII (2.13 grams, 95% yield).

Step 7: Synthesis of PST 2915.

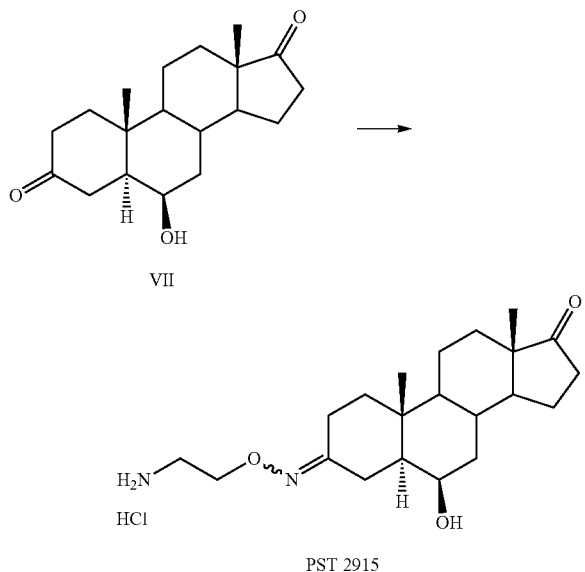

To a stirred solution of 6β-hydroxyandostane-3,17-dione VII (3.5 grams) in THF (100 mL), a solution of 2-aminoethoxyamine dihydrochloride (1.728 grams) in H$_2$O (34 mL) was rapidly added dropwise. After 1.5 h at room temperature under vigorous stirring, NaCl (4 grams) was added and the mixture stirred for 15 min. The phases were separated, and the aqueous phase was extracted twice with THF (2×50 mL). The combined organic extracts were dried over Na$_2$SO$_4$, filtered and evaporated to give a white solid (4.52 grams). The crude product was suspended and slurried in 45 mL of AcOEt/EtOH 97/3 for 1.5 hour then filtered and dried under reduce pressure at 35° C. for 48 hours, giving (E,Z)-3-(2-Aminoethoxyimino)-6beta-hydroxyandrostan-17-one hydrochloride, PST2915 (4.069 grams, 89% yield).

Synthesis of PST 3093
Step 1: Hydroboration.

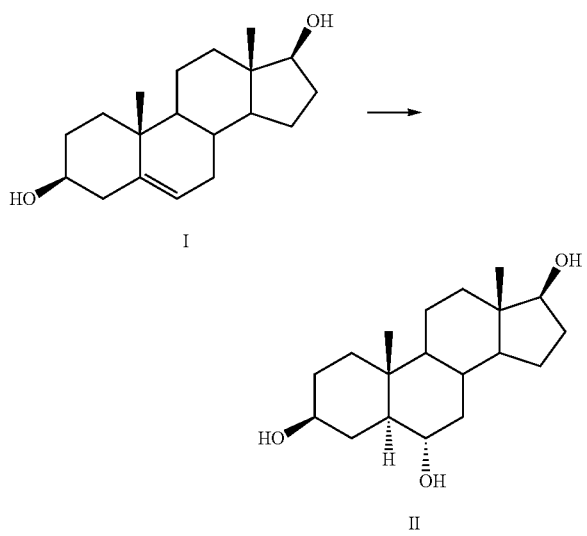

To a solution of dehydroepiandrosterone I (30.0 g) in 450 mL of anhydrous THF maintained under a nitrogen atmosphere and at a temperature of −10° C. was added the complex BH·THF 1M in THF (260 mL). On completing the addition, the temperature was allowed to rise once again to room temperature; after 3 hours, 500 mL of H$_2$O were added and then NaBO$_3$·4H$_2$O (31.4 g). The reaction was left to stir for one night. The precipitate formed was filtered, washed with THF and eliminated. The aqueous and organic phases were separated, NaCl was added to the aqueous phase and this was re-extracted with THF (3×200 mL). The combined organic phases were anhydrified with NaCl and Na$_2$SO$_4$ and evaporated under reduced pressure to obtain the crude product, which was crystallised by AcOEt/MeOH and then filtered and washed with AcOEt. Approximately 21 g of androstane 3β, 6α, 17β-triol II were obtained (known product: Nicholson, S. H., Turner, A. B. J. Chem. Soc., Perkin Trans. 1, 1976, 1357 and U.S. Pat. No. 6,384,250 B2).

The analytical results are in agreement with those reported in the literature.

Step 2: Selective Oxidation

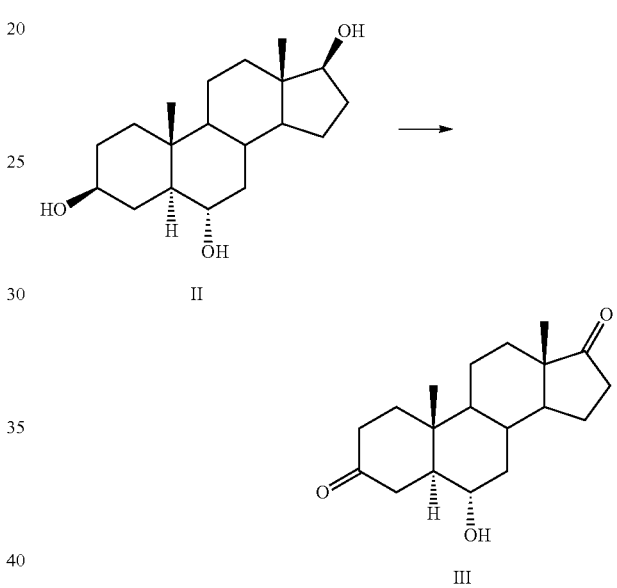

To a solution of Androstane 3β, 6α, 17β-triol II (30 grams) in a mixture composed by Dioxane (825 mL), Water (150 mL) and Pyridine (16.5 mL), N-Bromosuccinimide (52 grams) was added portion wise within 10 minutes protecting the vessel from light. The mixture was stirred for 16 hours at room temperature, diluted with 900 ml of water then Na$_2$S$_2$O$_3$ (15.5 grams) were added portion wise within 15 minutes. The solution was concentrated (around 1500 mL were removed) and the suspension was filtered and the solid dried under vacuum giving 28.1 grams of 6α-hydroxyandrostane-3,17-dione III (95% yield).

Step 3: Ketone Protection.

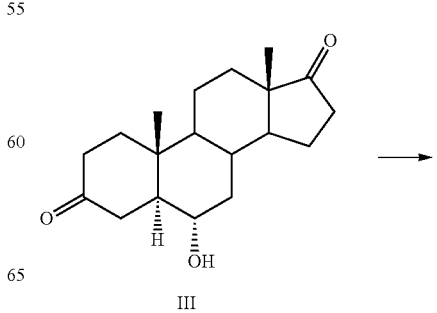

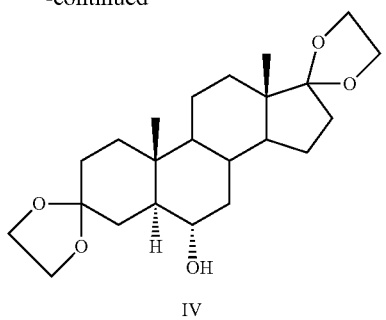

IV

A suspension of 6α-hydroxyandrostane-3,17-dione III (18.85 grams) in 360 mL of glycol and P-Toluenesulfonic Acid (554 mg) was heated at 100° C. and distilled under vacuum to remove the azeotropic mixture glycol/water (around 5 mL). The mixture was cooled and treated with 250 mg of KOH dissolved in 25 ml of Methanol. 15 mL of water were added and, after stirring for 2 hours, the suspension was filtered giving intermediate IV as white solid (20.2 grams, 83% yield). The product was used without further purification.

Step 4: Oxidation.

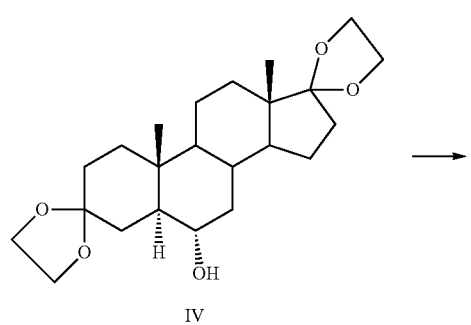

IV

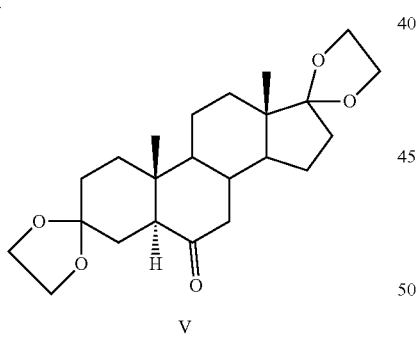

V

A solution constituted by 3 mL of Sodium Hypochlorite (6%) and 28 mL of Ethyl Acetate were stirred and 27 mg of $RuO_2$ hydrate were added. When all the catalyst Ruthenium was solubilized the product IV (1 gram) was added portion wise waiting for the disappearance of black suspension. After 1 hour additional 3 ml of Sodium Hypochlorite (6%) were added and the clear solution stirred for 3 hours at room temperature. When the reaction is completed the mixture was filtered on a Celite pad and the aqueous phase was extracted with AcOEt. The combined organic phases were washed with a solution of $NaHCO_3$ (5% in water) and with NaCl (10% in water). The organic layer was dried over $Na_2SO_4$ and evaporated to dryness giving intermediate V (950 mg, 94% yield).

Step 5: Reduction.

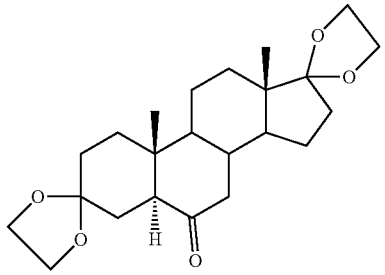

V

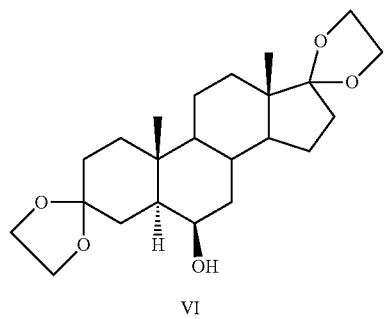

VI

A suspension of product V (5.76 grams) in Methanol (72 mL) was stirred at 0° C. and $NaBH_4$ (730 mg) was added. After 2 hours the reaction was completed, and the solvent was removed under reduced pressure. The crude product was suspended in 30 mL of water and extracted with $CH_2Cl_2$. The organic layer was separated and dried over $Na_2SO_4$ and evaporated to dryness. The crude solid was purified by flash chromatography ($SiO_2$, Cyclohexane/AcOEt 7/3 as eluent) giving the product VI (5.16 grams, 89% yield).

Step 6: Ketone Deprotection.

VI

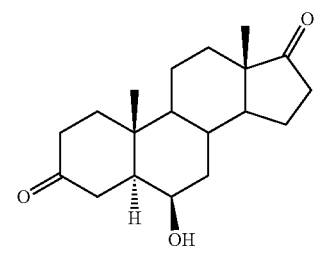

VII

To a stirred solution of product VI (2.85 grams) in 350 mL of distilled Acetone, P-toluenesulfonic acid (7.14 grams)

was added. After 3 hours at room temperature a 5% solution of NaHCO$_3$ was added and the solvent was removed under reduced pressure. The product was extracted with CH$_2$Cl$_2$. The organic layer was dried over Na$_2$SO$_4$ and evaporated to dryness, giving the intermediate VII (2.13 grams, 95% yield).

Step 7: Synthesis of PST 3093.

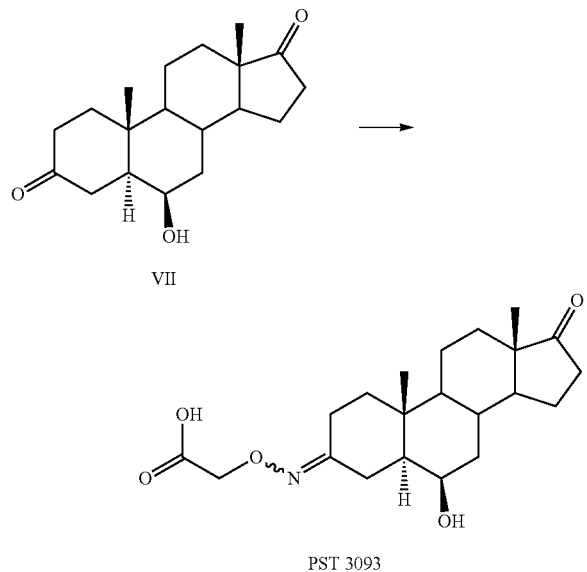

To a stirred solution of 6β-hydroxyandrostane-3,17-dione VII (4.5 grams) in THF (113 mL), a solution of O-(Carboxymethyl)hydroxylamine dihydrochloride (1.56 gram) in H$_2$O (5 mL) was rapidly added dropwise. After 1.5 h at room temperature under vigorous stirring, NaCl (6.4 grams) was added and the mixture stirred for 15 min. The phases were separated, and the aqueous phase was extracted three times with THF (50 mL). The combined organic extracts were dried over Na$_2$SO$_4$, filtered and evaporated to dryness giving 5.95 grams of crude product.

The crude product was purified by flash chromatography (SiO$_2$, CH$_2$Cl$_2$/MeOH/Acetic acid, 92.5/7/0.5) giving (E,Z)-[(6-beta-hydroxy-17-oxoandrostan-3-ylidene)amino]oxyacetic acid, PST3093 (3.7 grams, 69% yield).

Example 2. Biological Activity of Istaroxime Metabolites

Procedures
Animal Care

The investigation adheres to the Guide of the Care and Use of Laboratory Animals published by the National Institute of Health (NIH publication No. 85-23, revised 1996) and to the guidelines for animal care endorsed by the participating institutions.

Purification of Dog Renal Na,K-ATPase and Na,K-ATPase Activity Assay

Purification of renal Na,K-ATPase was performed according to the method of Jørgensen (Methods Enzymol. 1988; 156:29-43). Kidneys were excised from 1-3 year-old male beagle dogs (WuXi AppTec, Suzhou Co., Ltd. 1318 Wuzhong Ave., Wuzhong District Suzhou, 215104 P.R. China) under penthobarbital anesthesia (Import Authorization from Italian Health Ministry 0009171-09/04/2015-DGSAF-COD_UO-P, 2015). Kidneys were sliced and the outer medulla was dissected, pooled and suspended (1 g/10 ml) in a sucrose-histidine solution, containing 250 mM sucrose, 30 mM histidine and 5 mM EDTA, pH 7.2 and homogenized. The homogenate was centrifuged at 6.000 g for 15 min, the supernatant was decanted and centrifuged at 48.000 g for 30 min. The pellet was suspended in the sucrose-histidine buffer and incubated for 20 min with a sodium-dodecyl-sulphate (SDS) solution dissolved in a gradient buffer, containing 25 mM imidazole and 1 mM EDTA, pH 7.5. The sample was layered on the top of a sucrose discontinuous gradient (10, 15 and 29.4%) and centrifuged at 60.000 g for 115 min. The pellet was suspended in the gradient buffer.

Na,K-ATPase activity was assayed in vitro by measuring the release of $^{32}$P-ATP, as described previously (see Ferrandi M. et al., Hypertension 1996; 28(6):1018-25). Increasing concentrations of the standard ouabain, or tested compound, were incubated with 0.3 µg of purified dog kidney enzyme for 10 min at 37° C. in 120 µl final volume of a medium containing 140 mM NaCl, 3 mM MgCl$_2$, 50 mM Hepes-Tris, 3 mM ATP at a pH 7.5. Then, 10 µl of incubation solution containing 10 mM KCl and 20 nCi of $^{32}$P-ATP (3-10 Ci/mmol, Perkin Elmer) was added, and the reaction was continued for 15 min at 37° C. The reaction was then stopped by acidification with 20% v/v ice-cold perchloric acid. $^{32}$P was separated by centrifugation with activated Charcoal (Norit A, Serva) and the radioactivity was measured. The inhibitory activity was expressed as percent of the control samples carried out in the absence of ouabain or tested compound. The concentration of compound causing 50% inhibition of the Na,K-ATPase activity (IC$_{50}$) was calculated by using a multiple parameter non-linear regression best fitting program (Kaleidagraph™, Sinergy Software).

SERCA2a Activity Measurement in Heart Sarcoplasmic Reticulum (SR) Microsomes

Male beagle dogs were used for obtaining cardiac tissues for SERCA2a-enriched sarcoplasmic reticulum preparations. Healthy dogs were utilized for obtaining the data in Table 3. Chronic heart failure was induced in dogs by multiple intracoronary microembolizations with polystyrene latex microspheres (45-90 mm, Polysciences, Warrington, PA, USA) as described previously (see Sabbah H N et al., Am J Physiol. 1991; 260:H1379-84). The experiments were conducted in the General Pharmacology Department of Sigma-Tau, Rome, Italy.

Left ventricle tissues were dissected, homogenized in 4 volumes of 10 mM NaHCO$_3$ (pH 7), 1 mM PMSF, 10 µg/ml Aprotinin and Leupeptin and centrifuged at 12.000 g for 15 minutes, as described in Nediani C. et al. (J Biol Chem. 1996; 271:19066-73). Supernatants were filtered and centrifuged at 100.000 g for 30 min. Contractile proteins were extracted by suspending the pellets with 0.6 M KCl, 30 mM Histidine, pH 7 and further centrifugation at 100.000 g for 30 min. Final pellets were reconstituted with 0.3 M Sucrose, 30 mM Histidine, pH 7.

SERCA2a activity was measured in vitro as $^{32}$P-ATP hydrolysis at different Ca2$^+$ concentrations (100 to 3000 nM) in the absence and presence of the tested compounds as described previously (see Micheletti R. et al., Am J Card 2007; 99:24A-32A). Increasing concentrations of each compound (from 0.05 to 300 nM) were pre-incubated with 2 µg of microsomes for 5 min at 4° C. in 80 µl of a solution containing 100 mM KCl, 5 mM MgCl$_2$, 1 µM A23187, 20 mM Tris, pH 7.5. Then, 20 µl of 5 mM Tris-ATP containing 50 nCi of $^{32}$P-ATP (3-10 Ci/mmol, Perkin Elmer) was added. The ATP hydrolysis was continued for 15 min at 37°

C. and was stopped by acidification with 100 µl of 20% v/v ice-cold perchloric acid. $^{32}P$ was separated by centrifugation with activated charcoal (Norit A, SERVA) and the radioactivity was measured. SERCA2a-dependent activity was identified as the portion of total hydrolytic activity inhibited by 10 µM cyclopiazonic acid (see Seidler N W. et al., J Biol Chem. 1989; 264:17816-23).

Dose-response curves were fitted by using a sigmoidal curve fitting software and the maximal velocity (Vmax) activity and the Kd $Ca^{2+}$ were calculated (Synergy Software KaleidaGraph 3.6).

Drug Toxicity Studies in Mice

Acute toxicity has been determined in the mouse (Albino Swiss CD-1, body weight 30 g). Mice were orally treated, or intravenously injected, with single administration of increasing doses of the test substance to identify the dose causing 50% mortality. Mortality occurred within 30 min after the administration and survival after 24 h. The acute toxicity ($LD_{50}$) was then assessed.

Haemodynamics in streptozotocin diabetic rat (echocardiography 2M-Doppler-Tissue Doppler)

Sprague Dawley male rats (150-175 g) were made diabetic by a single injection into the tail vein of a solution of streptozotocin (STZ, 50 mg/kg, Sigma-Aldrich), freshly prepared in 0.1 M sodium citrate buffer, pH 4.5. Control rats received citrate buffer. Fasting glycaemia was measured after 1 week and rats with values greater than 400 mg/dl were considered diabetic.

Eight to nine weeks after STZ injection, rats were submitted to transthoracic echocardiographic and Doppler evaluation performed under pentobarbital anesthesia. Two-dimensionally guided M-mode recordings were used to obtain short-axis measurements of left ventricular end-diastolic diameter (LVEDD), left ventricular end-systolic diameter (LVESD), posterior (PW) and septal (SW) diastolic wall thickness according to the American Society of Echocardiography guidelines (Lang R M et al., Eur J Echocardiography 2006; 7:79-108). Fractional shortening was calculated as FS=(LVEDD-LVESD)/LVEDD. Relative wall thickness was calculated as PWTd+IVSTd/LVEDD.

Mitral inflow was measured by pulsed Doppler at the tips of mitral leaflets from an apical 4-chamber view to obtain early and late filling velocities (E, A) and deceleration time of early filling velocity (DT). The deceleration slope was calculated as E/DT ratio. The mitral deceleration index was calculated as DT/E ratio.

Tissue Doppler Imaging (TDI) was evaluated from the apical 4-chamber view to record septal mitral annular movements, i.e., peak myocardial systolic (s') and early and late diastolic velocity (e' and a').

The compound PST 3093 was iv administered to STZ injected rats at the dose of 0.22 mg/kg and echocardiographic parameters were measured after 15 and 30 min from the beginning of iv infusion and 10 min after interruption of infusion.

Statistical Analysis

Data are reported as mean & SD, as indicated. Statistical analysis was performed by Student's t-test (pair t test for STZ rats). P<0.05 was regarded as statistically significant.

Biological Results

In Vitro Screening

Inhibition of Dog Renal Na,K-ATPase Activity

Table 2 shows the inhibitory effect of the tested compounds on the enzymatic activity of the purified dog renal Na,K-ATPase. The corresponding $IC_{50}$ are expressed in µM concentration. Istaroxime inhibited the Na,K-ATPase activity with an $IC_{50}$ of 0.14 µM, similar to that of Digoxin, while PST 2915 inhibited the Na,K-ATPase activity with an $IC_{50}$ of 2.1 µM. Further, PST 3093 did not significantly inhibit Na,K-ATPase activity at all ($IC_{50}$>100 µM).

TABLE 2

Inhibition of dog renal Na, K-ATPase.

| Compound | $IC_{50}$, µM |
|---|---|
| DIGOXIN | 0.18 |
| ISTAROXIME | 0.14 |
| 3093 | >100 |
| 2915 | 2.1 |
| 2922 | >100 |

SERCA2a ATPase Activity in Heart-Derived SR Microsomes from Normal Dog

The compounds disclosed herein were tested on SERCA2a ATPase activity prepared from normal and failing dogs in a range of concentrations from 0.1 and 500 nM. The effect has been expressed as % increase of the Vmax activity of a control sample run in the absence of compound. Data are mean & SD, where n indicates the number of experiments.

In the normal dog SR vesicles, istaroxime, PST 3093 and PST 2915 significantly stimulated SERCA2a activity at concentrations of 0.1 nM and 10 nM (see Table 3). SERCA2a activation by istaroxime, PST 3093 and PST 2915 was also tested in failing dog preparations. This effect was particularly evident in the failing preparations (data not shown), where SERCA2a activity is known to be depressed compared to a normal heart (Bers D M, Physiology 2006; 21:380-387), and therefore implies that the compounds istaroxime and PST 3093 may correct SERCA2a alteration in the failing heart.

In contrast, previous studies showed that Digoxin failed to stimulate SERCA2a activity (Rocchetti M et al., J Pharmacol Exp Ther 2005; 313:207-215; Ferrandi M et al., Br J Pharmacol 2013; 169:1849-61).

TABLE 3

SERCA2a ATPase activity in heart-derived SR microsomes from normal dog. Data are expressed as % increase vs control and are mean ± SD

| Compound | Concentration nM (ng/ml) | Vmax (µmol/min/ mg prot) mean ± SD | % increase vs control *$p < 0.05$; **$p < 0.01$ |
|---|---|---|---|
| Istaroxime | 0 | 1.252 ± 0.083 (n = 5) | 0 |
| | 0.1 nM (0.039 ng/ml) | 1.423 ± 0.123 (n = 5) | 14* |
| | 10 nM (3.9 ng/ml) | 1.505 ± 0.111 (n = 5) | 20** |
| 3093 | 0 | 1.312 ± 0.050 (n = 5) | 0 |
| | 0.1 nM (0.037 ng/ml) | 1.641 ± 0.194 (n = 4) | 25** |
| | 10 nM (3.7 ng/ml) | 1.556 ± 0.106 (n = 4) | 19** |
| 2915 | 0 | 1.312 ± 0.050 (n = 5) | 0 |
| | 0.1 nM (0.041 ng/ml) | 1.464 ± 0.184 (n = 5) | 11 |
| | 10 nM (4.1 ng/ml) | 1.526 ± 0.038 (n = 5) | 16* |

TABLE 3-continued

SERCA2a ATPase activity in heart-
derived SR microsomes from normal dog.
Data are expressed as % increase vs
control and are mean ± SD

| Compound | Concentration nM (ng/ml) | Vmax (μmol/min/ mg prot) mean ± SD | % increase vs control *p < 0.05; **p < 0.01 |
|---|---|---|---|
| 2922 | 0 | 1.312 ± 0.050 (n = 5) | 0 |
|  | 0.1 nM (0.037 ng/ml) | 1.466 ± 0.112 (n = 5) | 12* |
|  | 10 nM (3.7 ng/ml) | 1.541 ± 0.170 (n = 5) | 17* |

In Vivo Studies

Acute Toxicity in Mouse

The acute toxicity of the tested compound PST 3093 was determined in the mouse (Albino Swiss CD-1, body weight 30 g). Compound PST 3093 was orally administered or intravenously injected at increasing doses to identify the dose causing 50% mortality. Mortality occurred within 30 min after the administration and survival after 24 h.

The results for PST 3093 acute toxicity are reported in Table 4 and indicated that the compound had an $LD_{50}$>250 and 200 mg/kg after iv or oral administration, respectively. For comparison, the acute toxicity for the reference compound istaroxime has been also included in Table 4.

TABLE 4

Acute toxicity ($LD_{50}$) of
Istaroxime and PS3093 in mouse.

| Compound | $LD_{50}$ mg/kg |
|---|---|
| Istaroxime i.v. | 29-32 |
| Istaroxime os | 200 |
| 3093 i.v. | >250 |
| 3093 os | >200 | i.v., intravenous
os, oral

Haemodynamics in Streptozotocin (STZ) Diabetic Rats (Echocardiography 2M-Doppler-Tissue Doppler)

Table 5 shows the echocardiographic parameters in STZ diabetic rats before and after 15 and 30 min from iv infusion of PST 3093 at 0.22 mg/kg, and 10 min after interruption of infusion. Data is presented as mean±SD, and values with an asterisk are statistically significant with at least p<0.05.

The data indicated that in an animal model characterized by a diastolic dysfunction, such as the STZ diabetic rats, PST 3093 administration ameliorated diastolic function. In particular, E wave (which represents the early filling velocity of transmitral inflow during the rapid filling phase and constitutes the energy dependent phase of LV relaxation, mainly mediated by SERCA2a activity) was significantly increased in STZ rats at 15 and 30 min after PST 3093 infusion (Table 5). This effect was consistent with a stimulation of SERCA2a activity by the compound, as shown in the in vitro assay (Table 3), suggesting the ability of PST 3093 to restore SERCA2a function activity, which is depressed in STZ rats as shown by Choi et al. (AJP 2002; H1398-H1408).

However, it should be considered that the peak E velocity is influenced by the preload and is directly correlated with heart rate (HR) (Mihm M J et al., Life Sci. 2001; 22; 69(5):527-42; do Carmo J M et al., AJP 2008; 295:H1974-1981). Conversely, the deceleration time of E wave (DT), and the related changes in mitral deceleration index (DT/E) and deceleration slope of E wave (E/DT), are not affected by HR changes and are considered robust indicators of diastolic function and early signs of diastolic dysfunction (Mihm M J et al., Life Sci. 2001; 22; 69(5):527-42). In particular, the behaviour of some echocardiographic diastolic parameters, such as the DT of E wave, can be affected even in opposite direction according to the various grades of diastolic dysfunction. As clearly indicated in previous publications (see Mitter S S et al., JACC 2017; 69(11):1451-1464), the DT of E wave is usually prolonged when diastolic dysfunction is of grade 1 and becomes very short in patients with grade 3 diastolic dysfunction, being dynamically affected also by the state of pulmonary congestion of the patient.

In this respect, the variation of the DT of E wave in animal models of diastolic dysfunction, as compared to the healthy controls, may vary in opposite directions. For example, in rats with diabetic cardiomyopathy induced by STZ injection, the DT results are equal to (see Thackeray J T et al., Cardiovasc Diabetol. 2011; 10:75; Carillion A et al., PloS One 2017; e0180103) or even longer than in control rats (Joffe I I et al., JACC Vol. 34, No. 7, 1999; 2111-2119; Guido M C et al., Oxid Med Cell Longev. 2017; 5343972); while in dogs with heart failure induced by microembolization of the coronary arteries, the DT results are reduced as compared with control healthy dogs (Sabbah H et al., Am J Cardiol. 2007; 99(2A):41A-46A). Furthermore, unlike transmitral Doppler flow, tissue-Doppler (TDI) parameters were relatively unaffected by load and a decrease in the early relaxation velocity (e') would be an unequivocal indicator of diastolic dysfunction.

The data evidenced marked effects of PST 3093 on these parameters. The E wave is significantly prolonged by PST 3093 treatment, while the DT is reduced. A significant reduction of DT and DT/E with increased of E/DT and e' are shown in Table 5. The increase of e' appeared to be associated with a significant increase of CO and SV, while no significant change of heart rate was observed. Of note, the direction of the effects of PST 3093 on DT and E/e' are the same as those obtained when this STZ rat model was treated with Istaroxime.

In contrast, in the HF dog model of coronary microembolization, where the DT was reduced as compared to control dogs (Sabbah H et al., Am J Cardiol. 2007; 99(2A): 41A-46A), the effect of istaroxime was to prolong the DT. In other words, independently from the variation of the DT of E wave in the HF animal models as compared with their respective controls, istaroxime reverses such parameters toward the levels present in the corresponding control animal and improves diastolic function.

These effects were more evident after 30 min from the beginning of PST 3093 infusion and tended to disappear after 10 min from the interruption of infusion. The effects of PST 3093 on the impaired cardiac function of STZ rats were consistent with the SERCA2a stimulatory activity of the compound that, by correcting the depressed cardiac relaxation, increased the amount of blood available for contraction and resulted in an increase of volume of blood pumped from the ventricle (SV).

To evaluate the relevance of the above results to the human condition, the obvious pathophysiological differences between the patients with AHF and the STZ rats should be considered. In the latter, marked changes in the body fluids, sympathetic nervous system and heart rate, may, per se, affect echocardiographic parameters, independently from the changes in cellular Ca$^{2+}$ handling and decrease of SERCA2a activity (Mihm M J et al., Life Sci. 2001; 22; 69(5):527-42; do Carmo J M et al., AJP 2008; 295:H1974-1981). Therefore, the similarities between human and rats in DT/E, E/DT and e' changes may be considered as having the same underlying mechanism—a stimulation of the SERCA2a activity by PST 3093.

TABLE 5

Haemodynamic parameters after 3093 iv infusion in STZ diabetic rats

| Function | Echo Parameter | STZ before (n = 10) | STZ 3093 0.22 mg/kg iv after 15 min (n = 10) | STZ 3093 0.22 mg/kg iv after 30 min (n = 10) | STZ 3093 after 10 min from STOP infusion (n = 8) |
|---|---|---|---|---|---|
| Diastolic function | E | 0.91 ± 0.197 | 1.048 ± 0.218* | 1.076 ± 0.211* | 0.89 ± 0.19 |
| | DT | 48.5 ± 12.01 | 40.2 ± 9.54 | 36.6 ± 6.09* | 41.88 ± 7.86* |
| | DT/E | 56.72 ± 20.46 | 40.39 ± 15.04* | 35.47 ± 10.19* | 49.08 ± 13.09* |
| | E/DT | 20.61 ± 9.91 | 27.51 ± 8.42* | 30.36 ± 8.73* | 22.36 ± 8.89* |
| | E/e' | 39.55 ± 5.43 | 38.61 ± 4.71 | 38.7 ± 4.26 | 39.45 ± 4.18 |
| | e' | 22.94 ± 3.35 | 27.01 ± 3.4* | 27.77 ± 4.27* | 22.48 ± 3.35 |
| overall | CO | 187.7 ± 43.35 | 231.7 ± 64* | 230.6 ± 46.7* | 200.88 ± 51.7 |
| | HR | 270 ± 54 | 271 ± 33 | 269 ± 29 | 249 ± 28 |
| | SV | 0.7 ± 0.15 | 0.85 ± 0.18* | 0.86 ± 0.14* | 0.81 ± 0.17* |

*P < 0.05 compared to basal values
E, E wave, early filling velocity of mitral inflow
DT (ms), deceleration time of E wave
DT/E (s$^2$/m), mitral deceleration index
E/DT (m/s$^2$), deceleration slope
E/e', index of LV filling pressure
e' (cm/s) TDI, early relaxation velocity
CO (ml/min), cardiac output
HR (beat/min), heart rate
SV (ml/beat), stroke volume

The invention claimed is:

1. A compound having a formula (III)

Formula (III)

PST 3093 or a pharmaceutically acceptable salt, ester, solvate, hydrate, or polymorph thereof.

2. A pharmaceutical composition comprising the compound of claim 1, or a pharmaceutically acceptable salt, solvate, hydrate, or polymorph thereof in an admixture with at least one pharmaceutically acceptable vehicle and/or excipient.

3. The pharmaceutical composition of claim 2, further comprising at least one additional therapeutic ingredient.

4. The pharmaceutical composition of claim 3, wherein the at least one additional therapeutic ingredient is selected from the group consisting of an ACE inhibitor, an AIRB, a diuretic, a Ca channel blocker, a beta-blocker, *digitalis*, an NO donor, a vasodilator, a SERCA2a stimulator, a neprilisin (NEP) inhibitor, a myosin filament activator, a recombinant relaxin-2 mediator, a recombinant NP protein, an activator of the soluble Guanylate Cyclase (sGC), and a beta-arrestin ligand of Angiotensin II receptor.

5. The pharmaceutical composition of claim 3, wherein the at least one additional therapeutic ingredient is selected from the group consisting of furosemide, bumetanide, torasemide, metolazone, spironolactone, eplerenone, hydrochlorothiazide, metolazone, chlorthalidone, lisinopril, ramipril, valsartan, candesartan, olmesartan, telmisartan, losartan, sacubitril, carvedilol, metoprolol, hydralazine, hydralazine combined with isosorbide dinitrate, nitroglycerin, isosorbide nitrate, amlodipine, felodipine, diltiazem, verapamil, Digoxin, entresto, omecantiv, serelaxin, ularitide, and levosimendan.

6. The pharmaceutical composition of claim 3, wherein the at least one additional therapeutic ingredient is in the same or in a separate unit dosage form of the compound having formula (III), or a pharmaceutically acceptable salt, solvate, hydrate, or polymorph thereof.

7. A method for treating an individual having heart failure, the method comprising the steps of:
(1) providing an individual having heart failure;
(2) administering to the individual a therapeutically effective amount of a pharmaceutical composition comprising (i) a pharmaceutically acceptable carrier; and (ii) istaroxime or a pharmaceutically acceptable salt, solvate, or hydrate thereof: wherein said administering comprises intravenous infusion for an infusion duration sufficient to produce in the individual a plasma concentration level of an istaroxime metabolite, wherein:
(i) the plasma concentration level is greater than about 5 ng/ml for an accumulation period longer than 6 hours; and
(ii) the istaroxime metabolite comprises the compound of claim 1; and
(3) measuring one or more parameters of heart function, wherein the one or more parameters of heart function comprises diastolic relaxation;
wherein the administering of the pharmaceutical composition results in an improvement in diastolic relaxation as compared to istaroxime administered by intravenous infusion prior to the accumulation period, thereby treating the individual having acute heart failure.

8. The method of claim 7, wherein the individual is human.

9. The method of claim 7, wherein the infusion duration is sufficient to produce in the individual a plasma concentration level of an istaroxime metabolite greater than about 10 ng/ml for an accumulation period longer than 6 hours.

10. The method of claim 7, wherein the infusion duration is sufficient to produce in the individual a plasma concentration level of an istaroxime metabolite greater than about 15 ng/ml for an accumulation period longer than 6 hours.

11. The method of claim 7, wherein the infusion duration is sufficient to produce in the individual a plasma concentration level of an istaroxime metabolite greater than about 20 ng/ml for an accumulation period longer than 6 hours.

12. A method for treating an individual having heart failure, the method comprising the steps of:
  (1) providing an individual having heart failure;
  (2) administering to the individual a therapeutically effective amount of a pharmaceutical composition comprising (i) a pharmaceutically acceptable carrier; and (ii) the compound of claim 1, wherein said administering comprises intravenous infusion;
  (3) measuring one or more parameters of heart function, wherein the one or more parameters of heart function comprises diastolic relaxation;
  wherein the administering of the pharmaceutical composition results in an improvement in diastolic relaxation, thereby treating the individual having acute heart failure.

13. The method of claim 12, wherein the compound is administered at a dose of about 0.2 mcg/kg/min to about 1.5 mcg/kg/min.

14. The method of claim 12, wherein the administering comprises intravenous infusion for an infusion duration selected from:
  at least about 6 hours;
  at least about 12 hours;
  at least about 24 hours;
  at least about 36 hours; and
  at least about 48 hours.

15. The method of claim 12, wherein the improvement in diastolic heart function is measured by echocardiography, a sphygmomanometer, an electrocardiogram, cardiac catheterization, a radionuclide ventriculography scan, or any combination thereof.

16. The method of claim 12, wherein the improvement in diastolic heart function comprises one or more of improved diastolic relaxation, increased diastolic blood pressure, decreased heart rate, a decrease in dyspnea, increased stroke volume, increased cardiac index, increased cardiac output, increased pulmonary capillary wedge pressure, or increased stroke volume index.

17. The method of claim 12, wherein the individual is human.

18. The method of claim 12, wherein the pharmaceutical composition further comprises at least one additional therapeutic ingredient.

19. The method of claim 18, wherein the at least one additional therapeutic ingredient is selected an ACE inhibitor, an AIRB, a diuretic, a Ca channel blocker, a beta-blocker, *digitalis*, an NO donor, a vasodilator, a SERCA2a stimulator, a neprilysin (NEP) inhibitor, a myosin filament activator, a recombinant relaxin-2 mediator, a recombinant NP protein, an activator of the soluble Guanylate Cyclase (sGC), and a beta-arrestin ligand of Angiotensin II receptor.

* * * * *